United States Patent
Galcera Contour et al.

(10) Patent No.: US 7,335,674 B2
(45) Date of Patent: *Feb. 26, 2008

(54) BENZOTHIAZOLE-4,7-DIONES AND BENZOXAZOLE-4,7-DIONES WITH SUBSTITUENTS IN POSITION 5 OR 6 AND METHOD FOR PRODUCTION THEREOF

(75) Inventors: Marie-Odile Galcera Contour, Bondoufle (FR); Olivier Lavergne, Palaiseau (FR)

(73) Assignee: Societe de Conseils de Recherches et d'Applications (S.C.R.A.S.), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/562,949

(22) PCT Filed: Jun. 24, 2004

(86) PCT No.: PCT/FR2004/001578

§ 371 (c)(1),
(2), (4) Date: Feb. 10, 2006

(87) PCT Pub. No.: WO2005/000843

PCT Pub. Date: Jan. 6, 2005

(65) Prior Publication Data

US 2006/0135573 A1    Jun. 22, 2006

(30) Foreign Application Priority Data

Jun. 25, 2003  (FR) .................................. 03 07648

(51) Int. Cl.
*A61K 31/423* (2006.01)
*A61K 31/438* (2006.01)
*C07D 277/64* (2006.01)
*C07D 277/66* (2006.01)
*C07D 263/56* (2006.01)
*C07D 263/57* (2006.01)

(52) U.S. Cl. ...................... 514/367; 514/375; 548/178; 548/217

(58) Field of Classification Search ................ 548/178, 548/217; 514/367, 375
See application file for complete search history.

(56) References Cited

FOREIGN PATENT DOCUMENTS

WO    WO 02/096348    12/2002
WO    WO 03/055868    7/2003

OTHER PUBLICATIONS

Lyon et al, 1999, J. Chem. Soc., Perkin Trans. I, p. 437-442.*
Golub et al, Oct. 15, 1999, Science, 286, p. 531-537.*
Hortobagyi, G., Oct. 1, 1998, N. Engl., J. Med, 339, 974-984.*
Chung-Kyu Ryu et al "5-Arylamino-2-methyl-4,7-dioxobenzothiazoles as Inhibitors of Cyclin-Dependent Kinase 4 and Cytotoxic Agents"Bioorganic & Medical Chemistry Letters, Oxford, GB, vol. 10, No. 5, Mar. 2000, pp. 461-464.

* cited by examiner

*Primary Examiner*—Rebecca Anderson
*Assistant Examiner*—Michael P. Barker
(74) *Attorney, Agent, or Firm*—Charles A. Muserlian

(57) ABSTRACT

A targetted production method for benzothiazole-4,7-dione and benzoxazole-4,7-dione derivatives, mono-substituted in the 5 or 6 position with an amino group, itself optionally substituted.

4 Claims, No Drawings

BENZOTHIAZOLE-4,7-DIONES AND BENZOXAZOLE-4,7-DIONES WITH SUBSTITUENTS IN POSITION 5 OR 6 AND METHOD FOR PRODUCTION THEREOF

This application is a 371 of PCT/FR 2004/001578 filed Jun. 24, 2004.

A subject of the present invention is certain derivatives of benzothiazole-4,7-diones and benzooxazole-4,7-diones substituted in position 5 or in position 6, which inhibit the Cdc25 phosphatases, in particular the Cdc25-C phosphatase, and/or the CD45 phosphatase as well as a process for the preparation of such derivatives and of the synthesis intermediates useful in the implementation of this process.

Control of the transition between the different phases of the cell cycle during mitosis or meiosis is ensured by a group of proteins the enzyme activities of which are associated with different states of phosphorylation. These states are controlled by two large classes of enzymes: the kinases and the phosphatases.

Synchronization of the different phases of the cell cycle thus allows reorganization of the cell architecture at each cycle in the whole of the living world (microorganisms, yeasts, vertebrates, plants). Among the kinases, the cyclin-dependent kinases (CDKs) play a major role in this control of the cell cycle. The enzyme activity of these different CDKs is controlled by two other families of enzymes which work in opposition (Jessus and Ozon, *Prog. Cell Cycle Res.* (1995), 1, 215-228). The first includes kinases such as Wee1 and Mik1 which deactivate the CDKs by phosphorylating certain amino acids (Den Haese et al., *Mol. Biol. Cell* (1995), 6, 371-385). The second includes phosphatases such as Cdc25 which activate the CDKs by dephosphorylating tyrosine and threonine residues of CDKs (Gould et al., *Science* (1990), 250, 1573-1576).

The phosphatases are classified in 3 groups: the serine/threonine phosphatases (PPases), the tyrosine phosphatases (PTPases) and the dual-specificity phosphatases (DSPases). These phosphatases play an important role in the regulation of numerous cell functions.

As regards human Cdc25 phosphatases, 3 genes (Cdc25-A, Cdc25-B and Cdc25-C) code for the Cdc25 proteins. Moreover, variants originating from alternative splicing of the Cdc25B gene have been identified (cf. for example Baldin et al., *Oncogene* (1997), 14, 2485-2495).

The role of the Cdc25 phosphatases in oncogenesis is now better known and the action mechanisms of these phosphatases are illustrated in particular in the following references: Galaktionov et al., *Science* (1995), 269, 1575-1577; Galaktionov et al., *Nature* (1996), 382, 511-517; and Mailand et al., *Science* (2000), 288, 1425-1429.

In particular, the overexpression of the different forms of Cdc25 is now reported in numerous series of human tumors:

Breast cancer: cf. Cangi et al., *Résumé* 2984, AACR meeting San Francisco, 2000);
Lymphomas: cf. Hernandez et al., *Int. J. Cancer* (2000), 89, 148-152 and Hernandez et al., *Cancer Res.* (1998), 58, 1762-1767;
Cancers of the neck and head: cf. Gasparotto et al., *Cancer Res.* (1997), 57, 2366-2368.
Cancer of the pancreas: cf. Junchao Guo et al., *Oncogene* (2004), 23, 71-81.

Moreover, E. Sausville's group reports an inverse correlation between the level of expression of Cdc25-B in a panel of 60 lines and their sensitivities to CDK inhibitors, suggesting that the presence of Cdc25 can bring a resistance to certain antineoplastic agents and more particularly to CDK inhibitors (Hose et al., *Proceedings of AACR, Abstract* 3571, San Francisco, 2000).

Among other targets, the pharmaceutical industry is therefore at present researching compounds capable of inhibiting the Cdc25 phosphatases in order to use them in particular as anti-cancer agents.

The Cdc25 phosphatases also play a role in neurodegenerative diseases such as Alzheimer's disease (cf. Zhou et al., *Cell Mol. Life Sci.* (1999), 56(9-10), 788-806; Ding et al., *Am. J. Pathol.* (2000), 157(6), 1983-90; Vincent et al., *Neuroscience* (2001), 105(3), 639-50) in such a manner that it is also possible to envisage using compounds possessing an inhibition activity on these phosphatases in order to treat these diseases.

Another problem addressed by the invention is research into medicaments intended to prevent or treat the rejection of organ transplants or also to treat auto-immune diseases. In these disorders/diseases, the non-appropriate activation of lymphocytes and monocytes/macrophages is involved. The immunosuppressive medicaments known at present have side effects which could be diminished or modified by products specifically targeting the signalling pathways in hematopoietic cells which initiate and maintain inflammation.

The CD45 phosphatase plays a crucial role in the transmission of signals from receptors on the T lymphocytes by regulating the phosphorylation and the activity of the tyrosine kinases of the src family, the negative regulation sites $p56^{lck}$ and $p59^{fyn}$ of which it is capable of dephosphorylating.

The CD45 phosphatase is therefore a potential target in the treatment of immune diseases. In fact, the blocking of the CD45 phosphatase by an anti-CD45 antibody inhibits the activation of the T lymphocytes in vitro (Prickett and Hart, *Immunology* (1990), 69, 250-256). Similarly, the T lymphocytes of transgenic mice not expressing CD45 (CD45 knock-out mice) do not correspond to stimulation by an antigen (Trowbridge and Thomas, *Annu. Rev. Immunol.* (1994), 12, 85-116).

Moreover, CD45 would be capable of dephosphorylating a sub-unit associated with Lyn, which would trigger a flow of calcium and activation of the mastocytes. Hamaguchi et al. (*Bioorg. Med. Chem. Lett.* (2000), 10, 2657-2660) have shown that a particular CD45 inhibitor (with an $IC_{50}$ equal to 280 nM) would suppress the release of histamine from rat peritoneal mastocytes and would protect mice from anaphylactic shock.

The advantage of finding CD45 phosphatase inhibitors would therefore appear obvious in particular when there is interest in:

obtaining an immunosuppressive effect in general, and in particular:
within the scope of the treatment of auto-immune diseases (Zong et al., *J. Mol. Med.* (1998), 76(8), 572-580) such as for example multiple sclerosis or autoimmune encephalitis (Yacyshyn et al., *Dig. Dis. Sci.* (1996), 41(12), 2493-8) and diabetes (Shimada et al., *J. Autoimmun.* (1996), 9(2), 263-269);
within the scope of the treatment of transplant rejections;
in the treatment of inflammation in general, and in particular:
within the scope of the treatment of arthritis (Pelegri et al., *Clin. Exp. Immunol.* (2001), 125(3), 470-477), rheumatoid arthritis, rheumatic diseases, conjunctivitis (Iwamoto et al., *Graefes Arch. Clin. Opthalmol.*(1999), 237(5), 407-414) and pruritic diseases;

within the scope of the treatment of digestive inflammatory diseases such as for example Crohn's disease (Yacyshyn et al., *Dig. Dis. Sci.*(1996), 41(12), 2493-2498), haemorrhagic rectocolitis and hepatitis (Volpes et al., *Hepatology* (1991), 13(5), 826-829); and in the treatment of allergies (Pawlik et al., *Tohoku J. Exp. Med.* (1997), 182(1), 1-8).

The invention offers novel Cdc25 phosphatase inhibitors (in particular Cdc25-C phosphatase inhibitors), and/or CD45 phosphatase inhibitors, which are derivatives of benzothiazole-4,7-diones and benzoxazole-4,7-diones corresponding to the general formulae (I), (II) and (III) defined hereafter. Given the above, these compounds are capable of being used as medicaments, in particular in the treatment of the following diseases/disorders:

inhibition of tumorous proliferation alone or in combination with other treatments;

inhibition of normal cell proliferation alone or in combination with other treatments;

neurodegenerative diseases such as Alzheimer's disease;

prevention of spontaneous alopecia;

prevention of alopecia induced by exogenous products;

prevention of radiation-induced alopecia;

prevention of spontaneous or induced apoptosis of normal cells;

prevention of meiosis and fertilization;

prevention of the maturation of oocytes;

all the diseases/all the disorders corresponding to uses reported for CDK inhibitors, and in particular non-tumorous proliferative diseases (for example: angiogenesis, psoriasis or restenosis), tumorous proliferative diseases, parasitology (proliferation of protozoans), viral infections, neurodegenerative diseases, myopathies;

all the diseases/all the disorders corresponding to clinical uses of vitamin K and its derivatives;

autoimmune diseases such as for example multiple sclerosis and rheumatoid arthritis; and diabetes.

Moreover, the compounds of the present invention are also, due to their Cdc25 phosphatase inhibition properties, capable of being used to inhibit the proliferation of microorganisms, in particular yeasts. One of the advantages of these compounds is their low toxicity on healthy cells.

A certain number of derivatives of benzothiazole-4,7-diones and benzoxazole-4,7-diones are already known.

In particular, the patent GB 1 534 275 relates to herbicides, the active ingredient of which is a compound corresponding to one of the general formulae

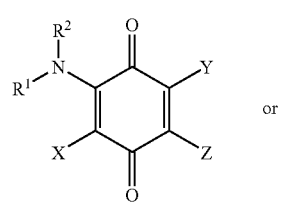

(A1) or

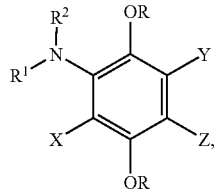

(A2)

in which:
R¹ represents in particular a hydrogen atom or an alkyl or cycloalkyl radical;
R² represents in particular a hydrogen atom, an alkyl or cycloalkyl radical;
X represents in particular a halogen atom or an alkoxy radical;
Y and Z can in particular represent together with the carbon atoms which carry them a thiazole ring optionally substituted by an alkyl radical; and
R represents in particular an alkyl radical.

Moreover, the Patent Application PCT WO 99/32115 described the compounds of general formula (A3)

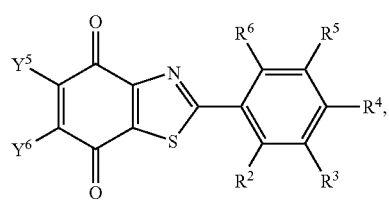

(A3)

in which:
the substituents R²-R⁶ are chosen from the group constituted by a hydrogen atom, electron-donating substituents, electron-attracting substituents and electron-modulating substituents;
and Y⁵ and Y⁶ are in particular chosen from the group constituted by a hydrogen atom, electron-donating substituents, electron-attracting substituents and electron-modulating substituents.

In the Patent Application PCT WO 99/32115, the term "electron-donating substituent" refers to a functional group having a tendency to donate electronic density; the substituents alkyl, alkenyl and alkynyl are mentioned. Throughout this Patent Application, "electron-attracting substituent" refers to a functional group having a tendency to attract electronic density; the substituents cyano, acyl, carbonyl, fluoro, nitro, sulphonyl and trihalomethyl are mentioned. Finally, an "electron-modulating substituent" is defined in this Application as a functional group having a tendency to modulate the electronic density, which can both attract and donate electrons and is therefore such that it can stabilize a cationic intermediate in an aromatic electrophilic substitution reaction; a functional group including, for example, amino substituents (for example —NH₂, alkylamino or dialkylamino), hydroxy, alkoxy or aryl, heterocyclic substituents, halogen atoms, etc. are mentioned.

The compounds of general formula (A3) are presented as modulators of the ryanodine receptors which can be used as pesticides or as therapeutic agents, for example in the treatment of congestive cardiac failure, migraine headaches, hypertension, Parkinson's disease or Alzheimer's disease or in the prevention of miscarriage.

Finally, the derivatives of benzooxazole-4,7-diones of general formula (A4)

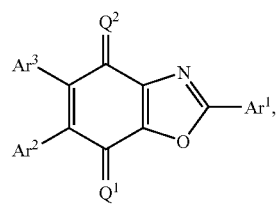

(A4)

in which:

Ar¹ represents an optionally substituted aryl radical, each of Ar² and Ar³ represents a hydrogen atom or an optionally substituted aryl radical, and each of Q¹ and Q² represents in particular O, are described as active constituents of photosensitive layers of photoreceptors.

In the Patent Application PCT/FR02/04544 (published under number WO 03/055868), the Applicant has described the compounds corresponding to general formula (I)

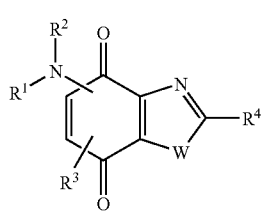

(I)

in which:

$R^1$ represents a hydrogen atom or an alkyl, alkoxyalkyl, alkylthioalkyl, cycloalkyl, —(CH$_2$)—X—Y, —(CH²)-Z-NR$^5$R$^6$ radical or a —CHR$^{35}$R$^{36}$ radical in which R$^{35}$ and R$^{36}$ form together with the carbon atom which carries them an indanyl or tetralinyl radical, or also R$^{35}$ and R$^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical, $R^1$ also being able, when W represents O, to represent moreover a carbocyclic aryl radical optionally substituted 1 to 3 times by substituents chosen independently from a halogen atom and an alkyl, haloalkyl or alkoxy radical, X representing a bond or a linear or branched alkylene radical containing 1 to 5 carbon atoms, Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle moreover containing 2 to 6 additional members chosen independently from —CHR$^7$—, —CO—, —NR$^8$—, —O— and —S—, R$^7$ representing a hydrogen atom or an alkyl radical and R$^8$ representing a hydrogen atom or an alkyl or aralkyl radical, or also Y representing a carbocyclic or heterocyclic aryl radical optionally substituted 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^9$ and an NR$^{10}$R$^{11}$ radical, R$^9$ representing a hydrogen atom or an alkyl or phenyl radical, and R$^{10}$ and R$^{11}$ independently representing alkyl radicals, Z representing a bond or a linear or branched alkylene radical containing 1 to 5 carbon atoms, $R^5$ and $R^6$ being chosen independently from a hydrogen atom, an alkyl, aralkyl or —(CH$_2$)$_n$—OH radical in which n represents an integer from 1 to 6, or R$^5$ representing an alkoxycarbonyl, haloalkoxycarbonyl or aralkoxycarbonyl radical and R$^6$ representing a hydrogen atom or a methyl radical, or also R$^5$ and R$^6$ forming together with the nitrogen atom a heterocycle with 4 to 7 members comprising 1 to 2 heteroatoms, the members necessary to complete the heterocycle being chosen independently from the —CR$^{12}$R$^{13}$—, —O—, —S— and —NR$^4$— radicals, R$^{12}$ and R$^{13}$ independently representing each time that they occur a hydrogen atom or an alkyl radical, and R$^{14}$ representing a hydrogen atom or an alkyl or aralkyl radical, or also R$^{14}$ representing a phenyl radical optionally substituted 1 to 3 times by substituents chosen independently from a halogen atom and an alkyl or alkoxy radical, $R^2$ representing a hydrogen atom or an alkyl or aralkyl radical;

or also R$^1$ and R$^2$ forming together with the nitrogen atom a heterocycle with 4 to 8 members comprising 1 to 2 heteroatoms, the members necessary to complete the heterocycle being chosen independently from the —CR$^{15}$R$^{16}$—, —O—, —S— and —NR$^{17}$— radicals, R$^{15}$ and R$^{16}$ independently representing each time that they occur a hydrogen atom or an alkyl radical, and R$^{17}$ representing a hydrogen atom or an alkyl or aralkyl radical;

$R^3$ represents a hydrogen atom, a halogen atom, or an alkyl, haloalkyl, alkoxy or alkylthio radical;

$R^4$ represents an alkyl, cycloalkyl, cycloalkylalkyl, cyano, amino, —CH$_2$—COOR$^{18}$, —CH$_2$—CO—NR$^{19}$R$^{20}$ or —CH²—NR$^{21}$R$^{22}$ radical, or R$^4$ represents a carbocyclic or heterocyclic aryl radical optionally substituted 1 to 4 times by substituents chosen independently from a halogen atom and an alkyl, haloalkyl, alkoxy, haloalkoxy or NR$^{37}$R$^{38}$ radical, or also R$^4$ represents a phenyl radical possessing two substituents which form together a methylenedioxy or ethylenedioxy radical, $R^{18}$ representing a hydrogen atom or an alkyl radical, $R^{19}$ representing a hydrogen atom, an alkyl radical or an aralkyl radical the aryl group of which is optionally substituted 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an SO$_2$NHR$^{23}$ radical and an NR$^{24}$R$^{25}$ radical, R$^{23}$ representing a hydrogen atom or an alkyl or phenyl radical, and R$^{24}$ and R$^{25}$ independently representing alkyl radicals, $R^{20}$ representing a hydrogen atom or an alkyl radical, or also R$^{19}$ and R$^{20}$ forming together with the nitrogen atom a heterocycle with 4 to 7 members comprising 1 to 2 heteroatoms, the members necessary to complete the heterocycle being chosen independently from the —$CR^{26}R^{27}$—, —O—, -S— and —$NR^{28}$— radicals, $R^{26}$ and $R^{27}$ independently representing each time that they occur a hydrogen atom or an alkyl radical, and $R^{28}$ representing a hydrogen atom or an alkyl or aralkyl radical, or also $R^{28}$ representing a phenyl radical optionally substituted 1 to 3 times by substituents chosen independently from a halogen atom and an alkyl or alkoxy radical, $R^{21}$ representing a hydrogen atom, an alkyl radical or an aralkyl radical the aryl group of which is optionally substituted 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^{29}$ radical and an $NR^{30}R^{31}$ radical, $R^{29}$ representing a hydrogen atom or an alkyl or phenyl radical, and $R^{30}$ and $R^{31}$ independently representing alkyl radicals, $R^{22}$ representing a hydrogen atom or an alkyl radical, or also $R^{21}$ and $R^{22}$ forming together with the nitrogen atom a heterocycle with 4 to 7 members comprising 1 to 2 heteroatoms, the members necessary to complete the heterocycle being chosen independently from the —$CR^{32}R^{33}$—, —O—, —S— and —$NR^{34}$— radicals, $R^{32}$ and $R^{33}$ independently representing each time that they occur a hydrogen atom or an alkyl radical, and $R^{34}$ representing a hydrogen atom, an alkyl or aralkyl radical, or also $R^{34}$ representing a phenyl radical optionally substituted 1 to 3 times by substituents chosen independently from a halogen atom and an alkyl or alkoxy radical, $R^{37}$ and $R^{38}$ being chosen independently from a hydrogen atom and an alkyl radical or $R^{37}$ and $R^{38}$ forming together with the nitrogen atom a heterocycle with 4 to 7 members comprising 1 to 2 heteroatoms, the members necessary to complete the heterocycle being chosen independently from the —$CR^{39}R^{40}$—, —O—, —S— and —$NR^{41}$— radicals, $R^{39}$ and $R^{40}$ independently representing each time that they occur a hydrogen atom or an alkyl radical, and $R^{41}$ representing a hydrogen atom or an alkyl radical; and W represents O or S;

and the pharmaceutically acceptable salts of compounds of general formula (I) defined above as Cdc25 phosphatase inhibitors, and in particular Cdc25-C phosphatase inhibitors, and/or CD45 phosphatase inhibitors. Said compounds can therefore be used for preparing a medicament intended to inhibit the Cdc25 phosphatases, and in particular the Cdc25-C phosphatase, and/or the CD45 phosphatase.

By alkyl, unless otherwise specified, is meant a linear or branched alkyl radical containing 1 to 12 carbon atoms, preferably 1 to 10 carbon atoms and more preferentially 1 to 8 carbon atoms (and in particular 1 to 6 carbon atoms). By cycloalkyl, unless otherwise specified, is meant a cycloalkyl radical containing 3 to 7 carbon atoms. By carbocyclic or heterocyclic aryl, is meant a carbocyclic or heterocyclic system with 1 to 3 condensed rings comprising at least one aromatic ring, a system being called heterocyclic when at least one of the rings which compose it comprises a heteroatom (O, N or S); when a carbocyclic or heterocyclic aryl radical is called substituted without further specification, it means that said carbocyclic or heterocyclic aryl radical is substituted 1 to 3 times, and preferably 1 to 2 times by radicals different from a hydrogen atom which, unless otherwise specified, are chosen from a halogen atom and the alkyl or alkoxy radicals; moreover, unless otherwise specified, by aryl is meant exclusively a carbocyclic aryl. By haloalkyl, is meant an alkyl radical at least one of the hydrogen atoms of which (and optionally all) is replaced by a halogen atom.

By cycloalkylalkyl, alkoxy, haloalkyl, haloalkoxy and aralkyl radicals, is meant respectively the cycloalkylalkyl, alkoxy, haloalkyl, haloalkoxy and aralkyl radicals, the alkyl, cycloalkyl and aryl radicals of which have the meanings indicated previously.

When it is indicated that a radical is optionally substituted 1 to 3 times, it is preferably optionally substituted 1 to 2 times and more preferentially optionally substituted once.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By haloalkyl, is meant in particular the trifluoromethyl radical. By haloalkoxy, is meant in particular the trifluoromethoxy radical. By carbocyclic aryl, is meant in particular the phenyl and naphthyl radicals. By aralkyl, is meant in particular the phenylalkyl radicals, and in particular the benzyl radical. By saturated carbon-containing cyclic system containing 1 to 3 condensed rings chosen independently from rings with 3 to 7 members, is meant in particular the cyclopropyl, cyclobutyl, cyclohexyl and adamantyl radicals. By heterocyclic or heteroaryl aryl, is meant in particular the thienyl, furanyl, pyrrolyl, imidazolyl, thiazolyl, oxazolyl and pyridyl radicals. Finally, by halogen, is meant fluorine, chlorine, bromine or iodine atoms.

By pharmaceutically acceptable salt, is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

In certain cases, the compounds according to the present invention can comprise asymmetrical carbon atoms. As a result, the compounds according to the present invention have two possible enantiomeric forms, i.e. the "R" and "S" configurations. The present invention includes the two enantiomeric forms and all combinations of these forms, including the "RS" racemic mixtures. In an effort to simplify matters, when no specific configuration is indicated in the structural formulae, it should be understood that the two enantiomeric forms and their mixtures are represented.

Four variants of the compounds of general formula (I) can be distinguished:

according to a first variant, the compounds of general formula (I) also correspond to general sub-formula (I)$_1$

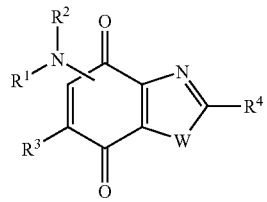

(I)$_1$ in which W represents S and $R^1$, $R^2$, $R^3$ and $R^4$ have the same meaning as in general formula (I);

according to a second variant, the compounds of general formula (I) also correspond to general sub-formula (I)$_2$

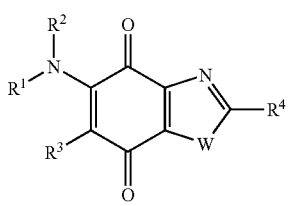

(I)$_2$ in which W represents O and R$^1$, R$^2$, R$^3$ and R$^4$ have the same meaning as in general formula (I);

according to a third variant, the compounds of general formula (I) also correspond to general sub-formula (I)$_3$

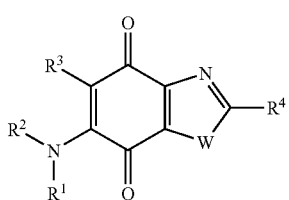

(I)$_3$ in which W represents S and R$^1$, R$^2$, R$^3$ and R$^4$ have the same meaning as in general formula (I); and according to a fourth variant, the compounds of general formula (I) also correspond to general sub-formula (I)$_4$

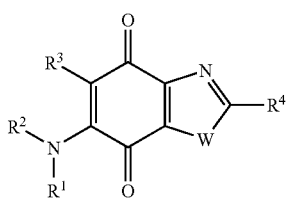

(I)$_4$ in which W represents O and R$^1$, R$^2$, R$^3$ and R$^4$ have the same meaning as in general formula (I).

The compounds of general formula (I)$_1$ or (I)$_2$, or their pharmaceutically acceptable salts can therefore be used for preparing a medicament intended to inhibit the Cdc25 phosphatases, and in particular the Cdc25-C phosphatase, and/or the CD45 phosphatase. Similarly, the compounds of general formula (I)$_3$ or (I)$_4$, or their pharmaceutically acceptable salts, can be used for preparing a medicament intended to inhibit the Cdc25 phosphatases, and in particular the Cdc25-C phosphatase, and/or the CD45 phosphatase.

Preferably, the compounds of general formula (I), (I)$_1$, (I)$_2$, (I)$_3$ or (I)$_4$ used for preparing a medicament intended to inhibit the Cdc25 phosphatases, and in particular the Cdc25-C phosphatase, include at least one of the following characteristics:

R$^1$ representing an alkyl, cycloalkyl, alkoxyalkyl, —(CH$_2$)—X—Y, —(CH$_2$)-Z-NR$^5$R$^6$ or —CHR$^{35}$R$^{36}$ radical;

R$^2$ representing a hydrogen atom or the methyl, ethyl or benzyl radical;

R$^1$ and R$^2$ forming together with the nitrogen atom a heterocycle with 4 to 8 members (preferably 5 to 7 members, and in particular 6 members) comprising 1 to 2 heteroatoms (and preferably 2 heteroatoms), the members necessary to complete the heterocycle being chosen independently from the —CH$_2$—, —O— and —NR$^{17}$ radicals (and preferably from the —CH$_2$— and —NR$^{17}$— radicals), R$^{17}$ representing a methyl or benzyl radical;

R$^3$ representing a hydrogen atom, a halogen atom or an alkyl, alkoxy or alkylthio radical;

R$^4$ representing an alkyl, —CH$_2$—COOR$^{18}$ or —CH$^2$—CO—NR$^{19}$R$^{20}$ or —CH$_2$—NR$^{21}$R$^{22}$ radical or also a carbocyclic or heterocyclic aryl radical optionally substituted 1 to 4 times (and in particular 1 to 3 times) by substituents chosen independently from a halogen atom and an alkyl, haloalkyl, alkoxy or NR$^{37}$R$^{38}$ radical.

Generally, for use for preparing a medicament intended to inhibit the Cdc25 phosphatases, and in particular the Cdc25-C phosphatase, the compounds of general formula (I) in which W represents a sulphur atom are preferred. Another useful alternative for use for preparing a medicament intended to inhibit the Cdc25 phosphatases, and in particular the Cdc25-C phosphatase, will nevertheless be the use of the compounds of general formula (I) in which W represents an oxygen atom.

Moreover, the X radical will preferably represent a bond or a linear alkylene radical containing 1 to 5 carbon atoms. Preferably also, the Y radical will represent a saturated carbon-containing cyclic system containing 1 to 3 condensed rings chosen independently from rings with 3 to 7 members, or Y will represent a carbocyclic aryl radical optionally substituted (preferably optionally substituted by 1 to 3 radicals chosen from a halogen atom and an alkyl, haloalkyl, alkoxy, haloalkoxy, SO$_2$NHR$^9$ or NR$^{10}$R$^{11}$ radical, and more preferentially optionally substituted by 1 to 3 radicals chosen from a halogen atom and an alkyl, alkoxy, SO$^2$NHR$^9$ or NR$^{10}$R$^{11}$ radical) or also Y will represent an optionally substituted heterocyclic aryl radical, said heterocyclic aryl radical being preferably chosen from the aryl radicals with 5 members (and in particular from the imidazolyl, thienyl or pyridinyl radicals) and preferably optionally substituted by 1 to 3 radicals chosen from a halogen atom and an alkyl, haloalkyl, alkoxy, haloalkoxy, SO$_2$NHR$^9$ or NR$^{10}$R$^{11}$ radical, and more preferentially optionally substituted by 1 to 3 radicals chosen from a halogen atom and an alkyl, alkoxy, SO$_2$NHR$^9$ or NR$^{10}$R$^{11}$ radical; R$^9$ will preferably represent a hydrogen atom and R$^{10}$ and R$^{11}$ will preferably represent radicals chosen independently from the alkyl radicals. The Z radical will preferably represent an alkylene radical containing 1 to 5 carbon atoms, and in particular a —(CH$_2$)$_p$— radical in which p represents an integer from 1 to 3 (p being preferably equal to 1 or 2 and more preferentially equal to 1). Preferably also, R$^5$ and R$^6$ are chosen independently from a hydrogen atom and an alkyl radical, or also R$^5$ and R$^6$ will form together with the nitrogen atom which carries them a heterocycle with 4 to 7 members comprising 1 to 2 heteroatoms, said heterocycle then being preferably one of the azetidinyl, pyrrolidinyl, piperidinyl, piperazinyl, homopiperazinyl, morpholinyl and thiomorpholinyl radicals optionally substituted by 1 to 3 alkyl radicals (and preferably by 1 to 3 methyl radicals); still more preferentially, R$^5$ and R$^6$ are chosen independently from alkyl or alkoxycarbonyl radicals (and in particular R$^5$ and R$^6$ are each a methyl radical or tert-butoxycarbonyl) or R$^5$ and R$^6$ will form together with the nitrogen atom which carries them a heterocycle with 4 to 7 members comprising 1 to 2 heteroatoms, said heterocycle being then preferably one of the azetidinyl, pyrrolidinyl, piperidinyl, piperazinyl, homopiperazinyl, morpholinyl and thiomorpholinyl radicals optionally substituted by 1 to 3 alkyl radicals (and preferably by 1 to 3 methyl radicals). $R^{18}$ will preferably represent a hydrogen atom or the methyl or ethyl radical.

Moreover, the $R^7$, $R^{12}$, $R^{13}$, $R^{15}$, $R^{16}$, $R^{26}$, $R^{27}$, $R^{39}$ and $R^{40}$ radicals are preferably chosen independently from a hydrogen atom and a methyl radical and the $R^8$, $R^{14}$, $R^{17}$, $R^{28}$ and $R^{41}$ radicals are preferably chosen independently from a hydrogen atom and a methyl or benzyl radical.

Moreover, with respect to $R^{19}$ and $R^{20}$, the cases will be preferred in which $R^{19}$ represents a hydrogen atom, an alkyl radical or a benzyl radical and $R^{20}$ represents a hydrogen atom or the methyl radical, as well as those in which $R^{19}$ and $R^{20}$ form together with the nitrogen atom which carries them a heterocycle with 4 to 7 members comprising 1 to 2 heteroatoms, said heterocycle then being preferably one of the azetidinyl, pyrrolidinyl, piperidinyl, piperazinyl, homopiperazinyl, morpholinyl and thiomorpholinyl radicals optionally substituted by 1 to 3 alkyl radicals (and preferably optionally substituted by 1 to 3 methyl radicals).

Moreover, with respect to $R^{21}$ and $R^{22}$, the cases will be preferred in which $R^{21}$ represents a hydrogen atom, an alkyl radical or a benzyl radical and $R^{22}$ represents a hydrogen atom or the methyl radical, as well as those in which $R^{21}$ and $R^{22}$ form together with the nitrogen atom which carries them a heterocycle with 4 to 7 members comprising 1 to 2 heteroatoms, said heterocycle then being preferably one of the optionally substituted azetidinyl, pyrrolidinyl, piperidinyl, piperazinyl, homopiperazinyl, morpholinyl and thiomorpholinyl radicals. With respect to the corresponding $R^{32}$, $R^{33}$ and $R^{34}$ radicals, these are preferably such that $R^{32}$ and $R^{33}$ are chosen independently from a hydrogen atom and an alkyl radical and preferably from a hydrogen atom and a methyl radical ($R^{32}$ and $R^{33}$ both representing still more preferentially hydrogen atoms) and that $R^{34}$ represents a hydrogen atom, an alkyl radical or a phenyl radical optionally substituted 1 to 3 times by substituents chosen independently from a halogen atom and an alkyl or alkoxy radical ($R^{34}$ representing still more preferentially a hydrogen atom or a methyl or phenyl radical).

Moreover, with respect to $R^{35}$ and $R^{36}$, the cases will be preferred in which $R^{35}$ and $R^{36}$ form together with the carbon atom which carries them an indanyl radical or $R^{35}$ and $R^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical.

Moreover, with respect to $R^{37}$ and $R^{38}$, the cases will be preferred in which $R^{37}$ and $R^{38}$ represent independently radicals chosen from the alkyl radicals.

Finally, when $R^4$ is a carbocyclic or heterocyclic aryl radical optionally substituted 1 to 4 times, it is preferable that it is chosen from the group consisting of carbocyclic and heterocyclic aryl radicals optionally substituted 1 to 3 times by substituents chosen independently from a halogen atom and an alkyl, haloalkyl, alkoxy, haloalkoxy or $NR^{37}R^{38}$ radical (and in particular 1 to 3 times by substituents chosen independently from a halogen atom and an alkyl, haloalkyl, alkoxy or haloalkoxy radical) and the 2,3,4,5-tetrafluorophenyl radical. More preferentially, when $R^4$ is a carbocyclic or heterocyclic aryl radical optionally substituted 1 to 4 times, $R^4$ is chosen from the group consisting of carbocyclic and heterocyclic aryl radicals optionally substituted 1 to 2 times by substituents chosen independently from a halogen atom, an alkyl, haloalkyl, alkoxy, haloalkoxy or $NR^{37}R^{38}$ radical (and in particular 1 to 2 times by substituents chosen independently from a halogen atom and an alkyl, haloalkyl, alkoxy or haloalkoxy radical), a 3,4,5-trihalophenyl radical and the 2,3,4,5-tetrafluorophenyl radical.

More preferentially, the compounds of general formula (I), (I)$_1$, (I)$_2$, (I)$_3$ or (I)$_4$ used for preparing a medicament intended to inhibit the Cdc25 phosphatases, and in particular the Cdc25-C phosphatase, include at least one of the following characteristics:
  $R^1$ representing an alkyl, cycloalkyl, or —(CH$_2$)-Z-NR$^5$R$^6$ radical;
  $R^2$ representing a hydrogen atom or the methyl radical;
  $R^3$ representing a hydrogen atom, a halogen atom or the methoxy radical;
  $R^4$ representing an alkyl, —CH$_2$—NR$^{21}$R$^{22}$ radical, or also a carbocyclic or heterocyclic aryl radical optionally substituted 1 to 4 times (and in particular 1 to 3 times) by substituents chosen independently from a halogen atom and an alkyl, or NR$^{37}$R$^{38}$ radical.

Also more preferentially, the compounds of general formula (I), (I)', (I)", (I)$_1$, (I)$_2$, (I)$_3$ or (I)$_4$ used according to the invention include at least one of the following characteristics:
  $R^1$ representing a —(CH$_2$)-Z-NR$^5$R$^6$ radical;
  $R^2$ representing a hydrogen atom;
  $R^3$ representing a hydrogen atom or a halogen atom (said halogen atom being preferably a chlorine or bromine atom);
  $R^4$ representing an alkyl radical or also a phenyl, pyridyl, thienyl or furanyl radical optionally substituted by 1 to 4 (preferably 1 to 3) halogen atoms or by an NR$^{37}$R$^{38}$ radical.

In still more particularly preferred fashion, the compounds of general formula (I), (I)$_1$, (I)$_2$, (I)$_3$ or (I)$_4$ used for preparing a medicament intended to inhibit the Cdc25 phosphatases, and in particular the Cdc25-C phosphatase, include at least one of the following characteristics:
  $R^3$ representing a hydrogen atom or a chlorine atom (and more preferentially a hydrogen atom);
  $R^4$ representing an alkyl radical or also a phenyl, pyridyl, thienyl or furanyl radical optionally substituted by 1 to 4 (preferably 1 to 3) halogen atoms (and in particular $R^4$ representing an alkyl radical, and preferably an alkyl radical containing 1 to 4 carbon atoms, and more preferentially also a methyl or ethyl radical).

According to a particular variant of the invention, W represents O. In this particular case, it is preferable that $R^1$ represents an aryl radical, and in particular a phenyl radical, optionally substituted 1 to 3 times by substituents chosen independently from a halogen atom and an alkyl, haloalkyl or alkoxy radical. More preferentially, whenever W represents O, it is preferable that $R^1$ represents a phenyl radical optionally substituted by a halogen atom (said halogen atom being preferably a fluorine atom).

According to a particular aspect of the invention, $R^4$ will represent a phenyl radical or a heterocyclic aryl radical with 5 to 6 members optionally substituted 1 to 4 times (and preferably 1 to 3 times) by substituents chosen from the group consisting of halogen atoms, the trifluoromethyl radical and the trifluoromethoxy radical (and preferably chosen from the group consisting of halogen atoms and the trifluoromethyl radical). In particular, said heterocyclic aryl with optionally substituted 5 to 6 members is an optionally substituted pyridine, thiophene, furan or pyrrole ring.

According to another particular aspect, compounds of general formula (I) in which W represents S, $R^3$ represents a hydrogen atom, the substituent —$NR^1R^2$ (the preferences indicated previously for $R^1$ and $R^2$ remaining applicable) is attached at position 5 of the benzothiazoledione ring and $R^4$ is chosen from the alkyl, cycloalkylalkyl, —$CH_2$—$COOR^{18}$, —$CH_2$—CO—$NR^{19}R^{20}$ and —$CH_2$—$NR^{21}R^{22}$ radicals ($R^4$ being preferably alkyl or cycloalkylalkyl and more preferentially alkyl according to this particular aspect of the invention) are used for preparing a medicament intended to inhibit the Cdc25 phosphatases, and in particular the Cdc25-C phosphatase.

Preferably, the compounds of general formula (I), $(I)_1$, $(I)_2$, $(I)_3$ or $(I)_4$ or their pharmaceutically acceptable salts are used for preparing a medicament intended to treat a disease chosen from the following diseases/the following disorders: tumorous proliferative diseases, and in particular cancer, non-tumorous proliferative diseases, neurodegenerative diseases, parasitic diseases, viral infections, spontaneous alopecia, alopecia induced by exogenous products, radiation-induced alopecia, auto-immune diseases, transplant rejections, inflammatory diseases and allergies.

Quite particularly, the compounds of general formula (I), $(I)_1$, $(I)_2$, $(I)_3$ or $(I)_4$ or their pharmaceutically acceptable salts can be used for preparing a medicament intended to treat cancer, and in particular breast cancer, lymphomas, cancers of the neck and head, lung cancer, cancer of the colon, prostate cancer and cancer of the pancreas.

According to a particular variant, the compounds of general formula (I), $(I)_1$, $(I)_2$, $(I)_3$ or $(I)_4$ or their pharmaceutically acceptable salts can be used for preparing a medicament intended to treat spontaneous alopecia, alopecia induced by exogenous products or radiation-induced alopecia.

A subject of the invention relates to a compound of general formula (II)

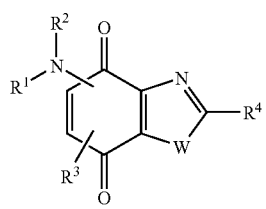

(II)

in which:
$R^1$ represents a hydrogen atom or an alkyl, alkoxyalkyl, alkylthioalkyl, cycloalkyl, —($CH_2$)-X-Y, —($CH_2$)-Z-$NR^5R^6$ radical or a —$CHR^{35}R^{36}$ radical in which $R^{35}$ and $R^{36}$ form together with the carbon atom which carries them an indanyl or tetralinyl radical, or also $R^{35}$ and $R^{36}$ form together with the carbon atom which carries them a saturated heterocycle containing 5 to 7 members and 1 to 2 heteroatoms chosen from O, N and S, the nitrogen atoms of said heterocycle being optionally substituted by radicals chosen from the alkyl radicals and the benzyl radical,
$R^1$ also being able, when W represents O, to represent moreover a carbocyclic aryl radical optionally substituted 1 to 3 times by substituents chosen independently from a halogen atom and an alkyl, haloalkyl or alkoxy radical,
X representing a bond or a linear or branched alkylene radical containing 1 to 5 carbon atoms,
Y representing a saturated carbon-containing cyclic system containing 1 to 3 condensed rings chosen independently from rings with 3 to 7 members, or Y representing a saturated heterocycle containing 1 to 2 heteroatoms chosen independently from O, N and S and attached to the X radical by an N or CH member, said saturated heterocycle containing moreover 2 to 6 additional members chosen independently from —$CHR^7$—, —CO—, —$NR^8$—, —O— and —S—, $R^7$ representing a hydrogen atom or an alkyl radical and $R^8$ representing a hydrogen atom or an alkyl or aralkyl radical, or also Y representing a carbocyclic or heterocyclic aryl radical optionally substituted 1 to 3 times by substituents chosen independently from the group constituted by a halogen atom, an alkyl radical, a haloalkyl radical, an alkoxy radical, a haloalkoxy radical, a hydroxy radical, a nitro radical, a cyano radical, the phenyl radical, an $SO_2NHR^9$ radical and an $NR^{10}R^{11}$ radical, $R^9$ representing a hydrogen atom or an alkyl or phenyl radical, and $R^{10}$ and $R^{11}$ independently representing alkyl radicals,
Z representing a bond or a linear or branched alkylene radical containing 1 to 5 carbon atoms,
$R^5$ and $R^6$ being chosen independently from a hydrogen atom, an alkyl, aralkyl or —($CH_2)_n$—OH radical in which n represents an integer from 1 to 6,
or $R^5$ representing an alkoxycarbonyl, haloalkoxycarbonyl or aralkoxycarbonyl radical and $R^6$ representing a hydrogen atom or a methyl radical,
or also $R^5$ and $R^6$ forming together with the nitrogen atom a heterocycle with 4 to 7 members comprising 1 to 2 heteroatoms, the members necessary to complete the heterocycle being chosen independently from the —$CR^{12}R^{13}$—, —O—, —S— and —$NR^{14}$— radicals, $R^{12}$ and $R^{13}$ independently representing each time that they occur a hydrogen atom or an alkyl radical, and $R^{14}$ representing a hydrogen atom or an alkyl or aralkyl radical, or also $R^{14}$ representing a phenyl radical optionally substituted 1 to 3 times by substituents chosen independently from a halogen atom and an alkyl or alkoxy radical,
$R^2$ representing a hydrogen atom or an alkyl or aralkyl radical;
or also $R^1$ and $R^2$ forming together with the nitrogen atom-a heterocycle with 4 to 8 members comprising 1 to 2 heteroatoms, the members necessary to complete the heterocycle being chosen independently from the —$CR^{15}R^{16}$—, —O—, —S— and —$NR^{17}$— radicals, $R^{15}$ and $R^{16}$ independently representing each time that they occur a hydrogen atom or an alkyl radical, and $R^{17}$ representing a hydrogen atom or an alkyl or aralkyl radical;
$R^3$ represents a hydrogen atom, a halogen atom, or an alkyl, haloalkyl, alkoxy or alkylthio radical;
$R^4$ represents a —$CH_2$—Ar radical in which Ar represents an aryl radical optionally substituted 1 to 4 times (and in particular 1 to 3 times) by substituents chosen independently from a halogen atom and an alkyl, haloalkyl, alkoxy, haloalkoxy or $NR^{42}R^{43}$ radical, or also R represents a biphenyl radical,
$R^{42}$ and $R^{43}$ being chosen independently from a hydrogen atom and an alkyl radical or $R^{42}$ and $R^{43}$ forming together with the nitrogen atom a heterocycle with 4 to 7 members comprising 1 to 2 heteroatoms, the members necessary to complete the heterocycle being chosen independently from the —$CR^{44}R^{45}$—, —O—, —S— and —$NR^{46}$— radicals, $R^{44}$ and $R^{45}$ independently representing each time that they occur a hydrogen atom or an alkyl radical, and $R^{46}$ representing a hydrogen atom or an alkyl radical;
and the salts of compounds of general formula (II) defined above These compounds can be used as Cdc25 phosphatase inhibitors, and in particular Cdc25-C phosphatase and/or CD45 phosphatase inhibitors.

The invention also relates, as medicaments, to the compounds of general formula (II) or their pharmaceutically acceptable salts. It relates moreover to pharmaceutical compositions comprising, as active ingredient, one of the compounds of general formula (II) or a pharmaceutically acceptable salt of the latter, as well as at least one pharmaceutically acceptable excipient.

A subject of the invention is also the use of the compounds of general formula (II) or their pharmaceutically acceptable salts for preparing a medicament intended to inhibit the Cdc25 phosphatases, and in particular the Cdc25-C phosphatase, and/or the CD45 phosphatase. Preferably, said compounds or their pharmaceutically acceptable salts are used for preparing a medicament intended to treat a disease chosen from the following diseases/the following disorders: tumorous proliferative diseases, and in particular cancer, non-tumorous proliferative diseases, neurodegenerative diseases, parasitic diseases, viral infections, spontaneous alopecia, alopecia induced by exogenous products, radiation-induced alopecia, auto-immune diseases, transplant rejections, inflammatory diseases and allergies. Quite particularly, said compounds or their pharmaceutically acceptable salts can be used for preparing a medicament intended to treat cancer, and in particular breast cancer, lymphomas, cancers of the neck and head, lung cancer, cancer of the colon, prostate cancer and cancer of the pancreas.

The preferences indicated above for the definitions of $R^1$, $R^2$, $R^3$ and W of the compounds of general formula (I) are applicable mutatis mutandis to the definitions of $R^1$, $R^2$, $R^3$ and W of the compounds of general formula (II).

Four variants of the compounds of general formula (II) can in particular be distinguished:

according to a first variant, the compounds of general formula (II) also correspond to general sub-formula $(II)_1$

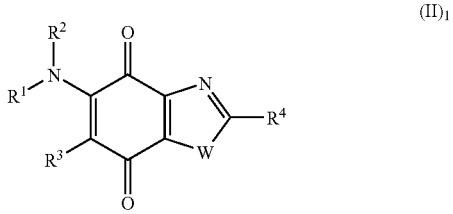

in which W represents S and $R^1$, $R^2$, $R^3$ and $R^4$ have the same meaning as in general formula (II);

according to a second variant, the compounds of general formula (II) also correspond to general sub-formula $(II)_2$

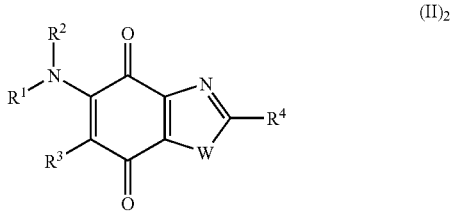

in which W represents O and $R^1$, $R^2$, $R^3$ and $R^4$ have the same meaning as in general formula (II);

according to a third variant, the compounds of general formula (II) also correspond to general sub-formula $(II)_3$

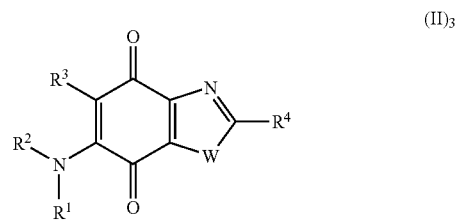

in which W represents S and $R^1$, $R^2$, $R^3$ and $R^4$ have the same meaning as in general formula (II); and according to a fourth variant, the compounds of general formula (II) also correspond to general sub-formula $(II)_4$

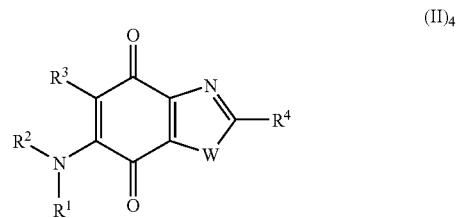

in which W represents O and $R^1$, $R^2$, $R^3$ and $R^4$ have the same meaning as in general formula (II).

Moreover, with respect to $R^4$, $R^4$ will represent a —$CH_2$—Ar radical according to one of the possible variants of the compounds of general formula (II). In this case, it will be preferable that $R^4$ represents a —$CH_2$—Ar radical in which Ar represents an aryl radical optionally substituted 1 to 4 times by substituents chosen independently from a halogen atom and an alkyl, haloalkyl, alkoxy or haloalkoxy radical. More preferentially, $R^4$ will represent a —$CH_2$—Ar radical in which Ar represents an aryl radical optionally substituted 1 to 4 times by substituents chosen independently from a halogen atom and an alkyl or haloalkyl radical. Also more preferentially, $R^4$ will represent a —$CH_2$—Ar radical in which Ar represents an aryl radical optionally substituted 1 to 4 times (in particular 1 to 3 times and more particularly 1 to 2 times) by halogen atoms (which are preferably chosen from chlorine and fluorine atoms).

According to another variant of the compounds of general formula (II), $R^4$ will represent a biphenyl radical, and in particular the 4-phenyl-phenyl radical.

According to the present invention, the following compounds of general formula (II):

2-(1,1'-biphenyl-4-yl)-6-{[2-(dimethylamino)ethyl]amino}-1,3-benzothiazole-4,7-dione;

2-benzyl-5-{[2-(dimethylamino)ethyl]aminol}-1,3-benzoxazole-4,7-dione;

2-(2,6-dichlorobenzyl)-6-{[2-(dimethylamino)ethyl]amino}-1,3-benzoxazole-4,7-dione;

2-(2-chloro-6-fluorobenzyl)-6-{[2-(dimethylamino)ethyl]amino}-1,3-benzoxazole-4,7-dione;

6-{[2-(dimethylamino)ethyl]amino}-2-(1-naphthylmethyl)-1,3-benzoxazole-4,7-dione;

2-(2-chloro-6-fluorobenzyl)-6-[(2-pyrrolidin-1-ylethyl)amino]-1,3-benzoxazole-4,7-dione;

as well as the salts of the latter will be preferred.

By definition, the compounds of general formula (III)

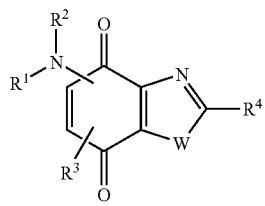

(III)

are such that $R^1$, $R^2$, $R^3$ and W are as defined in general formula (I) and $R^4$ is either as defined in general formula (I), or as defined in general formula (II).

The preferences indicated above for the definitions of $R^1$, $R^2$, $R^3$ and W of the compounds of general formula (I) or (II) are applicable mutatis mutandis to the definitions of $R^1$, $R^2$, $R^3$ and W of the compounds of general formula (III).

Four variants of the compounds of general formula (III) can in particular be distinguished:

according to a first variant, the compounds of general formula (III) also correspond to general sub-formula $(III)_1$

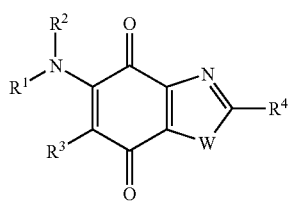

$(III)_1$ in which W represents S and $R^1$, $R^2$, $R^3$ and $R^4$ have the same meaning as in general formula (III);

according to a second variant, the compounds of general formula (III) also correspond to general sub-formula $(III)_2$

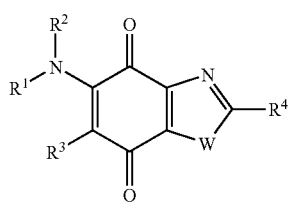

$(III)_2$ in which W represents O and $R^1$, $R^2$, $R^3$ and $R^4$ have the same meaning as in general formula (III);

according to a third variant, the compounds of general formula (III) also correspond to general sub-formula $(III)_3$

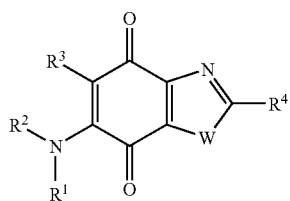

$(III)_3$ in which W represents S and $R^1$, $R^2$, $R^3$ and $R^4$ have the same meaning as in general formula (III); and according to a fourth variant, the compounds of general formula (III) also correspond to general sub-formula $(III)_4$

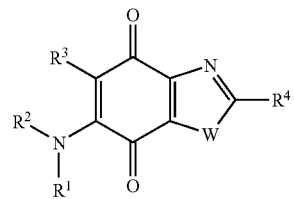

$(III)_4$ in which W represents O and $R^1$, $R^2$, $R^3$ and $R^4$ have the same meaning as in general formula (III).

In particular, the compounds of general formula (III), $(III)_1$, $(III)_2$, $(III)_3$ or $(III)_4$ which include at least one of the following characteristics are preferred:

$R^1$ representing an alkyl, cycloalkyl, alkoxyalkyl, —$(CH_2)$—X—Y, —$(CH_2)$-Z-$NR^5R^6$ or —$CHR^{35}R^{36}$ radical;

$R^2$ representing a hydrogen atom or the methyl, ethyl or benzyl radical;

$R^1$ and $R^2$ forming together with the nitrogen atom a heterocycle with 4 to 8 members (preferably 5 to 7 members, and in particular 6 members) comprising 1 to 2 heteroatoms (and preferably 2 heteroatoms), the members necessary to complete the heterocycle being chosen independently from the —$CH_2$—, —O— and —$NR^{17}$ radicals (and preferably from the —$CH_2$— and —$NR^{17}$— radicals), $R^{17}$ representing a methyl or benzyl radical;

$R^3$ representing a hydrogen atom, a halogen atom or an alkyl, alkoxy or alkylthio radical;

$R^4$ representing an alkyl, —$CH_2$—$COOR^{18}$ or —$CH_2$—CO—$NR^{19}R^{20}$ or —$CH_2$—$NR^{21}R^{22}$ radical, a carbocyclic or heterocyclic aryl radical optionally substituted 1 to 4 times (and in particular 1 to 3 times) by substituents chosen independently from a halogen atom and an alkyl, haloalkyl, alkoxy or $NR^{37}R^{38}$ radical or also $R^4$ representing a —$CH_2$—Ar radical in which Ar represents an aryl radical optionally substituted 1 to 4 times by substituents chosen independently from a halogen atom and an alkyl, haloalkyl, alkoxy or haloalkoxy radical.

The compounds of general formula (III), $(III)_1$, $(III)_2$, $(III)_3$ or $(III)_4$ which include at least one of the following characteristics are more particularly preferred:

$R^1$ representing a —$(CH_2)$-Z-$NR^5R^6$ radical;

$R^2$ representing a hydrogen atom;

$R^3$ representing a hydrogen atom or a halogen atom (said halogen atom being preferably a chlorine or bromine atom);

$R^4$ representing an alkyl radical or also a phenyl, pyridyl, thienyl or furanyl radical optionally substituted by 1 to 4 (preferably 1 to 3) halogen atoms or by an $NR^{37}R^{38}$ radical or also $R^4$ representing a —$CH_2$—Ar radical in which Ar represents a phenyl or naphthyl radical optionally substituted 1 to 4 times (and preferably 1 to 3 times) by substituents chosen independently from a halogen atom and an alkyl, haloalkyl, alkoxy or haloalkoxy radical.

The compounds of general formula (III), $(III)_1$, $(III)_2$, $(III)_3$ or $(III)_4$ which include at least one of the following characteristics are quite particularly preferred:

$R^3$ representing a hydrogen atom or a chlorine atom (and more preferentially a hydrogen atom);

$R^4$ representing an alkyl radical or also a phenyl, pyridyl, thienyl, furanyl, benzyl or naphthylmethyl radical optionally substituted by 1 to 4 (preferably 1 to 3) halogen atoms on the aromatic part of the radical.

Advantageously, the compounds of general formula (III), (III)$_1$, (III)$_2$, (III)$_3$ or (III)$_4$ (and in particular the compounds of general formula (I), (I)$_1$, (I)$_2$, (I)$_3$ or (I)$_4$ or the compounds of general formula (II), (II)$_1$, (II)$_2$, (II)$_3$ or (II)$_4$) can be prepared according to a selective preparation process. Said process makes it possible to substitute either position 5 or position 6 of the benzothiazole-4,7-dione or benzooxazole-4,7-dione nucleus and therefore to obtain a compound of general formula (III)$_1$ and not the corresponding compound of general formula (III)$_3$ (or vice versa), or also a compound of general formula (III)$_2$ and not the corresponding compound of general formula (III)$_4$ (or vice versa).

The invention therefore relates firstly to a process for the preparation of a compound of general formula (III)$_1$ or (III)$_2$ as defined previously in which $R^3$ represents a hydrogen atom, said process being characterized in that the compound of general formula (A)

(A)

in which W represents a sulphur atom or an oxygen atom and $R^4$ has the same meaning as in general formula (III)$_1$ or (III)$_2$ is reacted with an amine of general formula $R^1R^2NH$ in a protic solvent at a temperature preferably comprised between 20° C. and the boiling temperature of the solvent.

The invention relates in particular to a process for the preparation of a compound of general formula (I)$_1$ or (I)$_2$ as defined previously in which $R^3$ represents a hydrogen atom, said process being characterized in that the compound of general formula (A)

(A)

in which W represents a sulphur atom or an oxygen atom and $R^4$ has the same meaning as in general formula (I)$_1$ or (I)$_2$ is reacted with an amine of general formula $R^1R^2NH$ in a protic solvent at a temperature preferably comprised between 20° C. and the boiling temperature of the solvent.

Preferably, the protic solvent for the abovementioned processes is chosen from ethanol and methanol.

The invention also relates to a process for the preparation of a compound of general formula (III)$_3$ or (III)$_4$ as defined previously in which $R^3$ represents a hydrogen atom, said process being characterized in that the compound of general formula (K)

(K)

in which W represents a sulphur atom or an oxygen atom and $R^4$ has the same meaning as in general formula (III)$_3$ or (III)$_4$ is reacted with an amine of general formula $R^1R^2NH$ in a protic solvent at a temperature preferably comprised between 20° C. and the boiling temperature of the solvent.

The invention relates in particular to a process for the preparation of a compound of general formula (I)$_3$ or (I)$_4$ as defined previously in which $R^3$ represents a hydrogen atom, said process being characterized in that the compound of general formula (K)

(K)

in which W represents a sulphur atom or an oxygen atom and $R^4$ has the same meaning as in general formula (I)$_3$ or (I)$_4$ is reacted with an amine of general formula $R^1R^2NH$ in a protic solvent at a temperature preferably comprised between 20° C. and the boiling temperature of the solvent.

Preferably, the protic solvent for the abovementioned processes is chosen from ethanol and methanol.

The invention also relates, as novel products, to the compounds of general formula (A) in which W and $R^4$ have the meaning indicated previously, it being understood however that if W represents a sulphur atom then $R^4$ is not methyl, as well as the salts of the latter.

The invention thus relates in particular, as novel products, to the compounds of general formula (A) in which W represents an oxygen atom (hereafter respectively the compounds of general formula (A')), as well as the salts of the latter.

It similarly relates to the compounds of general formula (A) in which W represents a sulphur atom and $R^4$ has the meaning indicated previously but does not represent methyl (hereafter respectively the compounds of general formula (A")), as well as the salts of the latter. Preferably, the compounds of general formula (A") or their salts are such that $R^4$ has the meaning indicated previously but does not represent alkyl.

The invention also relates, as novel products, to the compounds of general formula (K) in which W and $R^4$ have the meaning indicated previously, it being understood however that if W represents a sulphur atom then $R^4$ is not the phenyl group (but can be a substituted phenyl group), as well as the salts of the latter.

The invention therefore in particular relates, as novel products, to the compounds of general formula (K) in which W represents an oxygen atom (hereafter respectively the compounds of general formulae (K')), as well as the salts of the latter.

It relates similarly to the compounds of general formula (K) in which W represents a sulphur atom and $R^4$ has the meaning indicated previously but does not represent the phenyl group (but can be a substituted phenyl group), compounds hereafter called the compounds of general formula (K"), as well as the salts of the latter. Preferably, the compounds of general formula (K") or their salts are such that $R^4$ represents a phenyl group substituted by at least one halogen atom or also such that $R^4$ represents an alkyl radical.

The invention also relates to the compounds of general formula (III) chosen from the following compounds:

2-(2,6-difluorophenyl)-5-{[2-(dimethylamino)ethyl] amino}-1,3-benzothiazole-4,7-dione;
2-(2,5-dichlorothien-3-yl)-5-{[2-(dimethylamino)ethyl] aminol}-1,3-benzothiazole-4,7-dione;
2-(2,5-dichlorothien-3-yl)-5-[(2-pyrrolidin-1-ylethyl) amino]-1,3-benzothiazole-4,7-dione;
5-{[2-(dimethylamino)ethyl]amino}-2-(4-fluorophenyl)-1,3-benzothiazole-4,7-dione;
2-(4-fluorophenyl)-5-[(2-pyrrolidin-1-ylethyl)amino]-1,3-benzothiazole-4,7-dione;
2-(2-chloro-6-fluorophenyl)-5-{[2-(dimethylamino)ethyl] amino}-1,3-benzothiazole-4,7-dione;
2-(2-chloro-6-fluorophenyl)-5-[(2-pyrrolidin-1-ylethyl) amino]-4,3-benzothiazole-4,7-dione;
6-{[2-(dimethylamino)ethyl]amino}-2-(4-fluorophenyl)-1,3-benzothiazole-4,7-dione;
6-{[2-(dimethylamino)ethyl]amino}-2-(1-naphthyl)-1,3-benzothiazole-4,7-dione;
2-(1,1'-biphenyl-4-yl)-6-{[2-(dimethylamino)ethyl]amino}-1,3-benzothiazole-4,7-dione;
2-(4-butylphenyl)-6-{[2-(dimethylamino)ethyl]amino}-1,3-benzothiazole-4,7-dione;
2-(2-chloro-6-fluorophenyl)-6-{[2-(dimethylamino)ethyl] amino}-1,3-benzothiazole-4,7-dione;
6-{[2-(dimethylamino)ethyl]amino}-2-(2-naphthyl)-1,3-benzothiazole-4,7-dione;
2-(2,5-difluorophenyl)-6-{[2-(dimethylamino)ethyl] amino}-1,3-benzothiazole-4,7-dione;
2-(2,5-difluorophenyl)-5-{[2-(dimethylamino)ethyl] amino}-1,3-benzoxazole-4,7-dione;
2-(2-bromophenyl)-5-{[2-(dimethylamino)ethyl]amino}-1,3-benzoxazole-4,7-dione;
2-(3-bromophenyl)-5-{[2-(dimethylamino)ethyl]amino}-1,3-benzoxazole-4,7-dione;
5-{[2-(dimethylamino)ethyl]amino}-2-(4-fluorophenyl)-1,3-benzoxazole-4,7-dione;
2-(3,5-difluorophenyl)-5-{[2-(dimethylamino)ethyl] amino}-1,3-benzoxazole-4,7-dione;
2-(2,3-difluorophenyl)-5-{[2-(dimethylamino)ethyl] amino}-1,3-benzoxazole-4,7-dione;
5-{[2-(dimethylamino)ethyl]amino}-2-(3,4,5-trifluorophenyl)-1,3-benzoxazole-4,7-dione;
5-{[2-(dimethylamino)ethyl]amino}-2-(4-ethylphenyl)-1,3-benzoxazole-4,7-dione;
2-benzyl-5-{[2-(dimethylamino)ethyl]amino}-1,3-benzoxazole-4,7-dione;
2-(3-bromophenyl)-5-[(2-pyrrolidin-1-ylethyl)amino]-1,3-benzoxazole-4,7-dione;
2-(3,5-difluorophenyl)-5-[(2-pyrrolidin-1-ylethyl)amino]-1,3-benzoxazole-4,7-dione;
5-[(2-pyrrolidin-1-ylethyl)amino]-2-(3,4,5-trifluorophenyl)-1,3-benzoxazole-4,7-dione;
2-(2,5-difluorophenyl)-6-{[2-(dimethylamino)ethyl] amino}-1,3-benzoxazole-4,7-dione;
2-(2-bromophenyl)-6-{[2-(dimethylamino)ethyl]amino}-1,3-benzoxazole-4,7-dione;
2-(3-bromophenyl)-6-{[2-(dimethylamino)ethyl]amino}-1,3-benzoxazole-4,7-dione;
2-(3-chlorophenyl)-6-{[2-(dimethylamino)ethyl]amino}-1,3-benzoxazole-4,7-dione;
2-(4-bromophenyl)-6-{[2-(dimethylamino)ethyl]amino}-1,3-benzoxazole-4,7-dione;
2-(3,5-dibromophenyl)-6-{[2-(dimethylamino)ethyl] amino}-1,3-benzoxazole-4,7-dione;
6-{[2-(dimethylamino)ethyl]amino}-2-(4-fluorophenyl)-1,3-benzoxazole-4,7-dione;
2-(3,5-difluorophenyl)-6-{[2-(dimethylamino)ethyl] amino}-1,3-benzoxazole-4,7-dione;
2-(2,3-difluorophenyl)-6-{[2-(dimethylamino)ethyl] amino}-1,3-benzoxazole-4,7-dione;
6-{[2-(dimethylamino)ethyl]amino}-2-(3,4,5-trifluorophenyl)-1,3-benzoxazole-4,7-dione;
2-(4-bromo-3-methylphenyl)-6-{[2-(dimethylamino)ethyl] amino}-1,3-benzoxazole-4,7-dione;
6-6-{[2-(dimethylamino)ethyl]amino}-2-(4-ethylphenyl)-1,3-benzoxazole-4,7-dione;
2-(4-bromo-2-chlorophenyl)-6-{[2-(dimethylamino)ethyl] amino}-1,3-benzoxazole-4,7-dione;
6-{[2-(dimethylamino)ethyl]amino}-2-(3,4,5-trimethoxyphenyl)-1,3-benzoxazole-4,7-dione;
2-(3,4-dimethoxyphenyl)-6-{[2-(dimethylamino)ethyl] amino}-1,3-benzoxazole-4,7-dione;
2-(2,6-dichlorobenzyl)-6-{[2-(dimethylamino)ethyl] amino}-1,3-benzoxazole-4,7-dione;
2-(2-chloro-6-fluorobenzyl)-6-{[2-(dimethylamino)ethyl] amino}-1,3-benzoxazole-4,7-dione;
6-{[2-(dimethylamino)ethyl]amino}-2-(1-naphthylmethyl)-1,3-benzoxazole-4,7-dione;
2-(2-bromophenyl)-6-[(2-pyrrolidin-1-ylethyl)amino]-1,3-benzoxazole-4,7-dione;
2-(3-bromophenyl)-6-[(2-pyrrolidin-1-ylethyl)amino]-1,3-benzoxazole-4,7-dione;
2-(3-chlorophenyl)-6-[(2-pyrrolidin-1-ylethyl)amino]-1,3-benzoxazole-4,7-dione;
2-(4-bromophenyl)-6-[(2-pyrrolidin-1-ylethyl)amino]-1,3-benzoxazole-4,7-dione;
2-(3,5-dibromophenyl)-6-[(2-pyrrolidin-1-ylethyl)amino]-1,3-benzoxazole-4,7-dione;
2-(4-fluorophenyl)-6-[(2-pyrrolidin-1-ylethyl)amino]-1,3-benzoxazole-4,7-dione;
2-(3,5-difluorophenyl)-6-[(2-pyrrolidin-1-ylethyl)amino]-1,3-benzoxazole-4,7-dione;
6-[(2-pyrrolidin-1-ylethyl)amino]-2-(3,4,5-trifluorophenyl)-1,3-benzoxazole-4,7-dione;
2-(4-bromo-3-methylphenyl)-6-[(2-pyrrolidin-1-ylethyl) amino]-1,3-benzoxazole-4,7-dione;
2-(4-ethylphenyl)-6-[(2-pyrrolidin-1-ylethyl)amino]-1,3-benzoxazole-4,7-dione;
2-(4-bromo-2-chlorophenyl)-6-[(2-pyrrolidin-1-ylethyl) amino]-1,3-benzoxazole-4,7-dione;
6-[(2-pyrrolidin-1-ylethyl)amino]-2-(3,4,5-trimethoxyphenyl)-1,3-benzoxazole-4,7-dione;
2-(3,4-dimethoxyphenyl)-6-[(2-pyrrolidin-1-ylethyl) amino]-1,3-benzoxazole-4,7-dione;

2-(2-chloro-6-fluorobenzyl)-6-[(2-pyrrolidin-1-ylethyl)
amino]-1,3-benzoxazole-4,7-dione;
2-(1,3-benzodioxol-5-yl)-6-[(2-pyrrolidin-1-ylethyl)
amino]-1,3-benzoxazole-4,7-dione;
6-{[2-(dimethylamino)ethyl]amino}-2-hexyl-1,3-benzothiazole-4,7-dione;

as well as the salts of the latter;

and in particular the following compounds of general formula (I):
2-(2,6-difluorophenyl)-5-{[2-(dimethylamino)ethyl]
amino}-1,3-benzothiazole-4,7-dione;
2-(2,5-dichlorothien-3-yl)-5-{[2-(dimethylamino)ethyl]
amino}-1,3-benzothiazole-4,7-dione;
2-(2,5-dichlorothien-3-yl)-5-[(2-pyrrolidin-1-ylethyl)
amino]-1,3-benzothiazole-4,7-dione;
5-{[2-(dimethylamino)ethyl]amino}-2-(4-fluorophenyl)-1,
3-benzothiazole-4,7-dione;
2-(4-fluorophenyl)-5-[(2-pyrrolidin-1-ylethyl)amino]-1,3-benzothiazole-4,7-dione;
2-(2-chloro-6-fluorophenyl)-5-{[2-(dimethylamino)ethyl]
amino}-1,3-benzothiazole-4,7-dione;
2-(2-chloro-6-fluorophenyl)-5-[(2-pyrrolidin-1-ylethyl)
amino]-1,3-benzothiazole-4,7-dione;

and the salts of the latter.

Among the abovementioned compounds of general formula (III) and their salts the following compounds are preferred:
2-(2,6-difluorophenyl)-5-{[2-(dimethylamino)ethyl]
amino}-1,3-benzothiazole-4,7-dione;
2-(2,5-dichlorothien-3-yl)-5-{[2-(dimethylamino)ethyl]
amino}-1,3-benzothiazole-4,7-dione;
2-(2,5-dichlorothien-3-yl)-5-[(2-pyrrolidin-1-ylethyl)
amino]-1,3-benzothiazole-4,7-dione;
5-{[2-(dimethylamino)ethyl]amino}-2-(4-fluorophenyl)-1,
3-benzothiazole-4,7-dione;
2-(4-fluorophenyl)-5-[(2-pyrrolidin-1-ylethyl)amino]-1,3-benzothiazole-4,7-dione;
2-(2-chloro-6-fluorophenyl)-5-{[2-(dimethylamino)ethyl]
amino}-1,3-benzothiazole-4,7-dione;
2-(2-chloro-6-fluorophenyl)-5-[(2-pyrrolidin-1-ylethyl)
amino]-1,3-benzothiazole-4,7-dione;
6-{[2-(dimethylamino)ethyl]amino}-2-(2-naphthyl)-1,3-benzothiazole-4,7-dione;
2-(2,5-difluorophenyl)-6-{[2-(dimethylamino)ethyl]
amino}-1,3-benzothiazole-4,7-dione;
2-(2,5-difluorophenyl)-5-{[2-(dimethylamino)ethyl]
amino}-1,3-benzoxazole-4,7-dione;
2-(2-bromophenyl)-5-{[2-(dimethylamino)ethyl]amino}-1,
3-benzoxazole-4,7-dione;
2-(3-bromophenyl)-5-{[2-(dimethylamino)ethyl]amino}-1,
3-benzoxazole-4,7-dione;
2-(2,3-difluorophenyl)-5-{[2-(dimethylamino)ethyl]
amino}-1,3-benzoxazole-4,7-dione;
2-(2,5-difluorophenyl)-6-{[2-(dimethylamino)ethyl]
amino}-1,3-benzoxazole-4,7dione;
2-(2-bromophenyl)-6-{[2-(dimethylamino)ethyl]amino}-1,
3-benzoxazole-4,7-dione;
2-(3-bromophenyl)-6-{[2-(dimethylamino)ethyl]amino}-1,
3-benzoxazole-4,7-dione;
2-(3-chlorophenyl)-6-{[2-(dimethylamino)ethyl]amino}-1,
3-benzoxazole-4,7-dione;
2-(4-bromophenyl)-6-{[2-(dimethylamino)ethyl]amino}-1,
3-benzoxazole-4,7-dione;
2-(3,5-dibromophenyl)-6-{[2-(dimethylamino)ethyl]
amino}-1,3-benzoxazole-4,7-dione;
2-(2,3-difluorophenyl)-6-{[2-(dimethylamino)ethyl]
amino}-1,3-benzoxazole-4,7-dione;
2-(4-bromo-3-methylphenyl)-6-{[2-(dimethylamino)ethyl]
amino}-1,3-benzoxazole-4,7-dione;
6-{[2-(dimethylamino)ethyl]amino}-2-(4-ethylphenyl)-1,3-benzoxazole-4,7-dione;
2-(4-bromo-2-chlorophenyl)-6-{[2-(dimethylamino)ethyl]
amino}-1,3-benzoxazole-4,7-dione;
6-{[2-(dimethylamino)ethyl]amino}-2-(3 4,5-trimethoxyphenyl)-1,3-benzoxazole-4,7-dione;
2-(3,4-dimethoxyphenyl)-6-{[2-(dimethylamino)ethyl]
amino}-1,3-benzoxazole-4,7-dione;
2-(2,6-dichlorobenzyl)-6-{[2-(dimethylamino)ethyl]
amino}-1,3-benzoxazole-4,7-dione;
2-(2-bromophenyl)-6-[(2-pyrrolidin-1-ylethyl)amino]-1,3-benzoxazole-4,7-dione;
2-(3-bromophenyl)-6-[(2-pyrrolidin-1-ylethyl)amino]-1,3-benzoxazole-4,7-dione;
2-(3-chlorophenyl)-6-[(2-pyrrolidin-1-ylethyl)amino]-1,3-benzoxazole-4,7-dione;
2-(4-bromophenyl)-6-[(2-pyrrolidin-1-ylethyl)amino]-1,3-benzoxazole-4,7-dione;
2-(3,5-dibromophenyl)-6-[(2-pyrrolidin-1-ylethyl)amino]-1,3-benzoxazole-4,7-dione;
2-(4-fluorophenyl)-6-[(2-pyrrolidin-1-ylethyl)amino]-1,3-benzoxazole-4,7-dione;
2-(3,5-difluorophenyl)-6-[(2-pyrrolidin-1-ylethyl)amino]-1,
3-benzoxazole-4,7-dione;
6-[(2-pyrrolidin-1-ylethyl)amino]-2-(3,4,5-trifluorophenyl)-1,3-benzoxazole-4,7-dione;
2-(4-bromo-3-methylphenyl)-6-[(2-pyrrolidin-1-ylethyl)
amino]-1,3-benzoxazole-4,7-dione;
2-(4-ethylphenyl)-6-[(2-pyrrolidin-1-ylethyl)amino]-1,3-benzoxazole-4,7-dione;
2-(4-bromo-2-chlorophenyl)-6-[(2-pyrrolidin-1-ylethyl)
amino]-1,3-benzoxazole-4,7-dione;
6-[(2-pyrrolidin-1-ylethyl)amino]-2-(3,4,5-trimethoxyphenyl)-1,3-benzoxazole-4,7-dione;
2-(3,4-dimethoxyphenyl)-6-[(2-pyrrolidin-1-ylethyl)
amino]-1,3-benzoxazole-4,7-dione;
2-(1,3-benzodioxol-5-yl)-6-[(2-pyrrolidin-1-ylethyl)
amino]-1,3-benzoxazole-4,7-dione;

as well as the salts of the latter.

Among the abovementioned compounds of general formula (III) and their salts, the following compounds are particularly preferred:
2-(2,6-difluorophenyl)-5-{[2-(dimethylamino)ethyl]
amino}-1,3-benzothiazole-4,7-dione;
5-{[2-(dimethylamino)ethyl]amino}-2-(4-fluorophenyl)-1,
3-benzothiazole-4,7-dione;
2-(4-fluorophenyl)-5-[(2-pyrrolidin-1-ylethyl)amino]-1,3-benzothiazole-4,7-dione;
2-(2-chloro-6-fluorophenyl)-5-{[2-(dimethylamino)ethyl]
amino}-1,3-benzothiazole-4,7-dione;
6-{[2-(dimethylamino)ethyl]amino}-2-(2-naphthyl)-1,3-benzothiazole-4,7-dione;
2-(2,5-difluorophenyl)-6-{[2-(dimethylamino)ethyl]
amino}-1,3-benzothiazole-4,7-dione;
2-2bromophenyl)-5-{[2-(dimethylamino)ethyl]amino}-1,3-benzoxazoe-4,7-dione;
2-(2,3-difluorophenyl)-5-{[2-(dimethylamino)ethyl]
amino}-1,3-benzoxazole-4,7-dione;
2-(2,5-difluorophenyl)-6-{[2-(dimethylamino)ethyl]
amino}-1,3-benzokazole-4,7-dione;
2-(2-bromophenyl)-6-{[2-(dimethylamino)ethyl]amino}-1,
3-benzoxazole-4,7-dione;

2-(3-bromophenyl)-6-{[2-(dimethylamino)ethyl]amino}-1,3-benzoxazole-4,7-dione;
2-(3-chlorophenyl)-6-{[2-(dimethylamino)ethyl]amino}-1,3-benzoxazole-4,7-dione;
2-(4-bromophenyl)-6-{[2-(dimethylamino)ethyl]amino)}-1,3-benzoxazole-4,7-dione;
2-(2,3-difluorophenyl)-6-{[2-(dimethylamino)ethyl]amino}-1,3-benzoxkazble-4,7-dione;
6-{[2-(diimethylamino)ethyl]amino}-2-(4-ethylphenyl)-1,3-benzoxazole-4,7-dione;
2-(2,6-dichlorobenzyl)-6-{[2-(dimethylamino)ethyl]amino}-1,3-benzoxazole-4,7-dione;
2-(2-bromophenyl)-6-[(2-pyrrolidin-1-ylethyl)amino]-1,3-benzoxazole-4,7-dione;
2-(3-bromophenyl)-6-[(2-pyrrolidin-1-ylethyl)amino]-1,3-benzoxazole-4,7-dione;
2-(4-bromophenyl)-6-[(2-pyrrolidin-1-ylethyl)amino]-1,3-benzoxazole-4,7-dione;
2-(4-fluorophenyl)-6-[(2-pyrrolidin-1-ylethyl)amino]-1,3-benzoxazole-4,7-dione;
2-(3,5-difluorophenyl)-6-[(2-pyrrolidin-1-ylethyl)amino]-1,3-benzoxazole-4,7-dione;
2-(4-bromo-2-chlorophenyl)-6-[(2-pyrrolidin-1-ylethyl)amino]-1,3-benzoxazole-4,7-dione;
2-(1,3-benzodioxol-5-yl)-6-[(2-pyrrolidin-1-ylethyl)amino]-1,3-benzoxazole-4,7-dione;

as well as the salts of the latter.

Among the abovementioned compounds of general formula (III) and their salts, the following compounds are more particularly preferred:
2-(2-chloro-6-fluorophenyl)-5-{[2-(dimethylamino)ethyl]amino}-1,3-benzothiazole-4,7-dione;
6-{[2-(dimethylamino)ethyl]amino}-2-(2-naphthyl)-1,3-benzothiazole-4,7-dione;
6-{[2-(dimethylamino)ethyl]amino}-2-(4-ethylphenyl)-1,3-benzoxazole-4,7-dione;

as well as the salts of the latter.

The invention also relates, as medicaments, to said compounds of general formula (I), (II) or (III) or their pharmaceutically acceptable salts. It relates moreover to the pharmaceutical compositions comprising, as active ingredient, one of said compounds of general formula (I), (II) or (III) or a pharmaceutically acceptable salt of the latter, as well as at least one pharmaceutically acceptable excipient.

A subject of the invention is also the use of said compounds of general formula (I), (II) or (III) or their pharmaceutically acceptable salts for preparing a medicament intended to inhibit the Cdc25 phosphatases, and in particular the Cdc25-C phosphatase, and/or the CD45 phosphatase. Preferably, said compounds or their pharmaceutically acceptable salts are used for preparing a medicament intended to treat a disease chosen from the following diseases/the following disorders: tumorous proliferative diseases, and in particular cancer, non-tumorous proliferative diseases, neurodegenerative diseases, parasitic diseases, viral infections, spontaneous alopecia, alopecia induced by exogenous products, radiation-induced alopecia, auto-immune diseases, transplant rejections, inflammatory diseases and allergies. Quite particularly, said compounds or their pharmaceutically acceptable salts can be used for preparing a medicament intended to treat cancer, and in particular breast cancer, lymphomas, cancers of the neck and head, lung cancer, cancer of the colon, prostate cancer and cancer of the pancreas.

The compounds of the invention (i.e. the compounds of general formula (I), $(I)_1$, $(I)_2$, $(I)_3$ or $(I)_4$, (II), $(II)_1$, $(II)_2$, $(II)_3$ or $(II)_4$ or (III), $(III)_1$, $(III)_2$, $(III)_3$ or $(III)_4$) can also be used in a treatment method for tumorous proliferative diseases, and in particular cancer, non-tumorous proliferative diseases, neurodegenerative diseases, parasitic diseases, viral infections, spontaneous alopecia, alopecia induced by exogenous products, radiation-induced alopecia, auto-immune diseases, transplant rejections, inflammatory diseases and allergies, said method comprising the administration of a therapeutically effective dose of a compound of general formula (I), $(I)_1$, $(I)_2$, $(I)_3$ or $(I)_4$, (II), $(II)_1$, $(II)_2$, $(II)_3$ or $(II)_4$ or (III), $(III)_1$, $(III)_2$, $(III)_3$ or $(III)_4$ to the patient needing this treatment.

The pharmaceutical compositions containing a compound of the invention (i.e. a compound of general formula (I), $(I)_1$, $(I)_2$, $(I)_3$ or $(I)_4$, (II), $(II)_1$, $(II)_2$, $(II)_3$ or $(II)_4$ or (III), $(III)_1$, $(III)_2$, $(III)_3$ or $(III)_4$) can be presented in the form of solids, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention (i.e. a compound of general formula (I), $(I)_1$, $(I)_2$, $(I)_3$ or $(I)_4$, (II), $(II)_1$, $(II)_2$, $(II)_3$ or $(II)_4$ or (III), $(III)_1$, $(III)_2$, $(III)_3$ or $(III)_4$) can also be presented in liquid form, for example, solutions, emulsions, suspensions or syrups. Appropriate liquid supports can be, for example, water, organic solvents such as glycerol or the glycols, as well as their mixtures, in varying proportions, in water.

The administration of a medicament according to the invention can be carried out by topical, oral, parenteral route, by intramuscular injection, etc.

The administration dose envisaged for a compound of general formula (I), $(I)_1$, $(I)_2$, $(I)_3$ or $(I)_4$, (II), $(II)_1$, $(II)_2$, $(II)_3$ or $(II)_4$ or (III), $(III)_1$, $(III)_2$, $(III)_3$ or $(III)_4$ is comprised between 0.1 mg to 10 g depending on the type of active compound used.

For the medicaments, pharmaceutical compositions and uses according to the invention, the preferences indicated for the compounds of general formulae (I), (II) and (III) are of course applicable mutatis mutandis.

The compounds of general formula (I), (II) and (III) can be prepared by the processes described hereafter.

Preparation of the Compounds of Formula (I), (II) and (III)

The preparation processes hereafter are given by way of illustration and a person skilled in the art can subject them to the variations that he deems useful, both with respect to the reagents and to the reaction conditions and techniques.

According to the present invention, the processes hereafter can be used in order to obtain exclusively a compound of general formula (III), and not the corresponding compound of general formula $(III)_3$ (or vice versa), or also a compound of general formula $(III)_2$ and not the corresponding compound of general formula $(III)_4$ (or vice versa). This process can evidently be used mutatis mutandis in order to regioselectively obtain the compounds of general formula (I) and (II). Only the processes for obtaining the compounds of general formula (III) are therefore described hereafter.

A) Process for the Preparation of the Regioisomers of General Formula $(III)_1$ or $(III)_2$ Generally, the compounds of general formula $(III)_1$ or $(III)_2$ in which $R^3$ represents H can be prepared according to the method illustrated in Diagram 1 hereafter.

Diagram 1

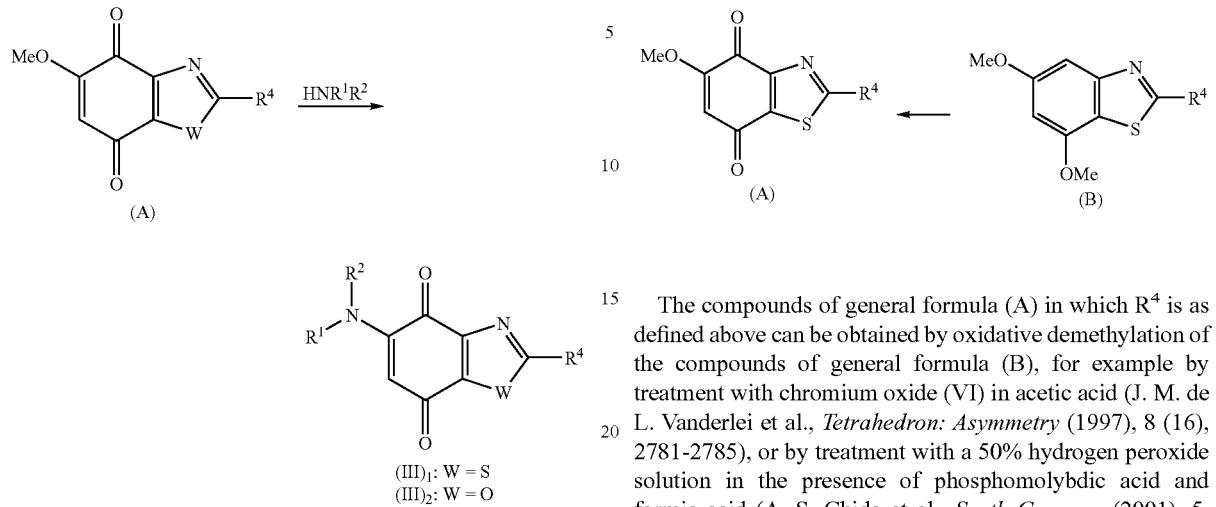

According to this method, the compounds of general formula (III)$_1$ or (III)$_2$, in which W, R$^1$, R$^2$ and R$^4$ are as defined above and R$^3$ represents H, are obtained by treatment of the compounds of general formula (A) with amines of general formula R$^1$R$^2$NH in a protic solvent such as methanol or ethanol, at a temperature preferably comprised between 25° C. and the boiling temperature of the solvent (Yasuyuki Kita et al., *J. Org. Chem.* (1996), 61, 223-227).

In the case where it is also desired to substitute position 6 of the benzothiazoledione or benzoxazoledione nucleus (compounds of general formula (III)$_1$ or (III)$_2$ in which R$^3$≠H), it is sufficient to carry out an additional substitution using the conditions familiar to a person skilled in the art.

i) W Represents a Sulphur Atom:

Preparation of the Intermediates of General Formula (A)

When W represents a sulphur atom, the intermediates of general formula (A) can be prepared according to the process represented in Diagram 2 hereafter.

The compounds of general formula (A) in which R$^4$ is as defined above can be obtained by oxidative demethylation of the compounds of general formula (B), for example by treatment with chromium oxide (VI) in acetic acid (J. M. de L. Vanderlei et al., *Tetrahedron: Asymmetry* (1997), 8 (16), 2781-2785), or by treatment with a 50% hydrogen peroxide solution in the presence of phosphomolybdic acid and formic acid (A. S. Chida et al., *Synth Commun* (2001), 5, 657-660), or also by treatment with dichlorodicyanoquinone (DDQ) in an H$_2$O/THF mixture (K. Narayanan, *Heterocycles* (1991), 10, 2005-2014) or also by treatment with cerium ammonium nitrate in an equimolar acetonitrile/water or ethyl acetate/water mixture under vigorous stirring at ambient temperature.

The nitrated compound of general formula (B.i) can be obtained by treatment of the compound of general formula (B) with cerium ammonium nitrate (CAN). The compound of general formula (A) can then be obtained after reduction of the nitro group by the action of hydrogen in the presence of palladium on carbon or by the action of tin chloride in order to obtain the intermediate of general formula (B.ii) which is then oxidized in order to finally produce the quinone of general formula (A) by the action of cerium ammonium nitrate (cf. Diagram 3 hereafter; K. Mohri et al., *Chem Pharm Bull,* (1998), 12, 1872-1877).

Diagram 2

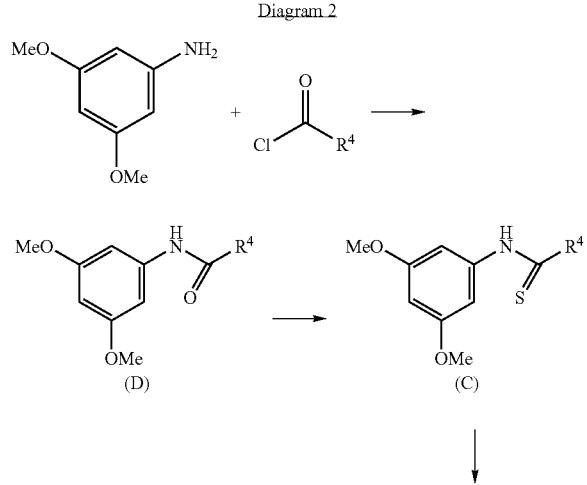

Diagram 3

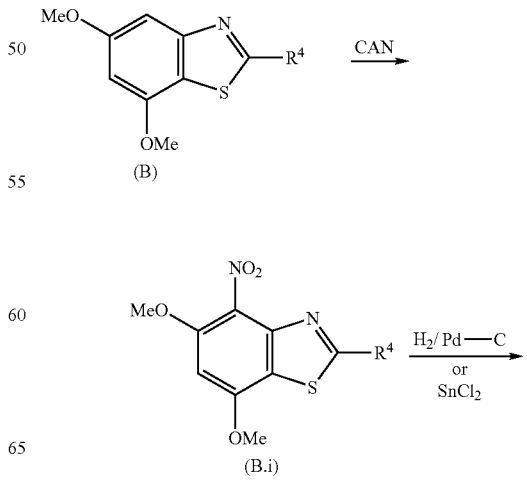

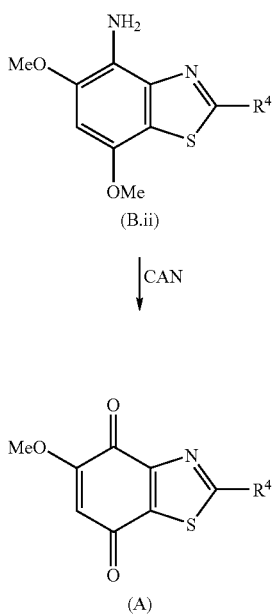

Preparation of the Intermediates of General Formula (B)

The compounds of general formula (B), in which $R^4$ is as defined above, can be obtained in 3 stages (M. A. Lyon et al., *J. Chem. Soc., Perkin Trans* 1, (1999), 437-442) from 3,5-dimethoxyaniline converted successively to amide (D) by the action of the corresponding acid chloride according to standard methods known to a person skilled in the art. The amides of general formula (D) are then converted to thioamides of general formula (C) by treatment with Lawesson's reagent in dry toluene at a temperature preferably comprised between 80° C. and reflux for a duration preferably comprised between 2 hours and 18 hours, or by potassium pentasulphide in DME at a temperature preferably comprised between 85° C. and reflux. The thioamides of general formula (C) are then treated with potassium ferricyanide in aqueous medium in the presence of soda according to the method of Jacobson (P. Jacobson, *Chem. Ber.* (1886), 19, 1067) in order to produce the compounds of general formula (B).

ii) W Represents an Oxygen Atom:

Preparation of the Intermediates of General Formula (A)

When W represents an oxygen atom, the intermediates of general formula (A) can be prepared according to the process represented in Diagram 4 below.

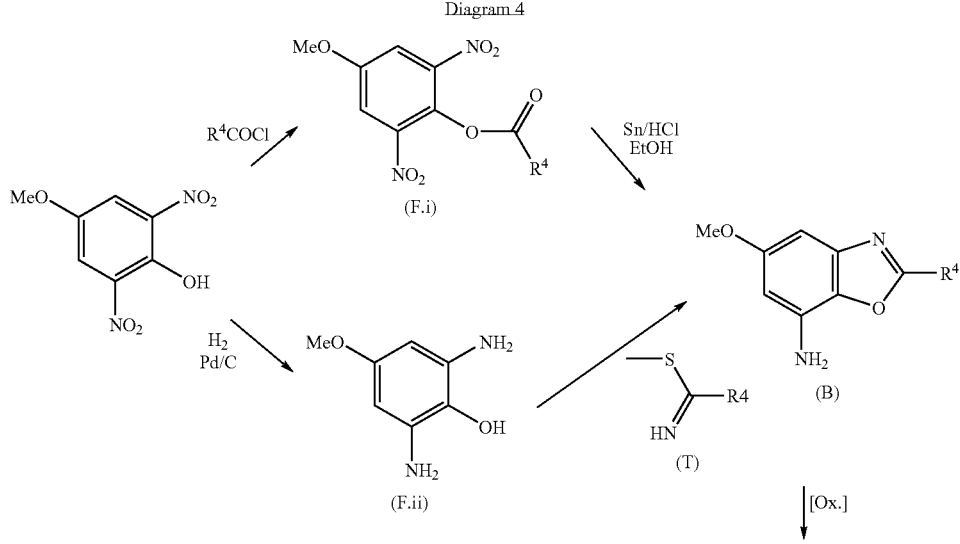

Diagram 4

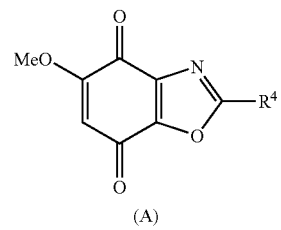

The compounds of general formula (A), in which $R^4$ is as defined above, can be obtained in 3 stages from 4-methoxy-2,6-dinitrophenol (described in particular by P. Cotelle and J.-P. Catteau, *Synth. Commun.*, 26, (1996), 4105-4112), which, once esterified in order to produce the intermediate of general formula (F.i) according to the usual methods known to a person skilled in the art can be subjected to the action of a reducing agent under dehydrating conditions (such as, for example, tin and hydrogen chloride in ethanol described by Y. A. M. Marghlani et al. *Pakistan J. Sci. Ind. Res.*, 23, (1980), 166-168) in order to provide a 7-amino-5-methoxy-benzoxazole derivative of general formula (E). Alternatively, 4-methoxy-2,6-dinitrophenol can be reduced, for example by the action of hydrogen in the presence of palladium on carbon, then without isolating the intermediate (F.ii), can be condensed with a thioimidate of general formula (T) in a protic solvent such as ethanol at a temperature comprised between 25° C. and the boiling temperature of the solvent (according to the method described in particular by S. Rostamizadeh et al. *J. Chem Res, Synop*, 6, (2001), 227-228) in order to provide the 7-amino-5-methoxy-benzoxazole derivative of general formula (E). The thioimidates of general formula (T) are commercial or are prepared by methods known to a person skilled in the art. The 7-amino function of the compound of general formula (E) then allows its oxidation to be achieved in order to produce the compound of general formula (A) according to processes described previously.

It is also possible to envisage the preparation of intermediates of general formula (A) in which W represents an oxygen atom according to the process described in Diagram 4a hereafter.

According to the alternative synthesis presented in Diagram 4a, 4-methoxy-2-nitrophenol (commercial) is converted to 5-methoxy-benzoxazole derivative of general formula (H), either by dehydrating esterification/reduction of Diagram 4, or by reduction followed by condensation described previously. The intermediate of general formula (H) is then nitrated and reduced to the corresponding amine according to a method already described above (cf. Diagram 3), then oxidized as previously to the quinone of general formula (A).

B) Process for the Preparation of the Regioisomers of General Formula (III)$_3$ or (III)$_4$ Generally, the compounds of general formula (III)$_3$ or (III)$_4$ in which $R^3$ represents H can be prepared according to the method illustrated in Diagram 5 hereafter.

Diagram 5

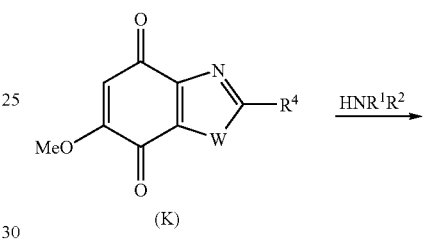

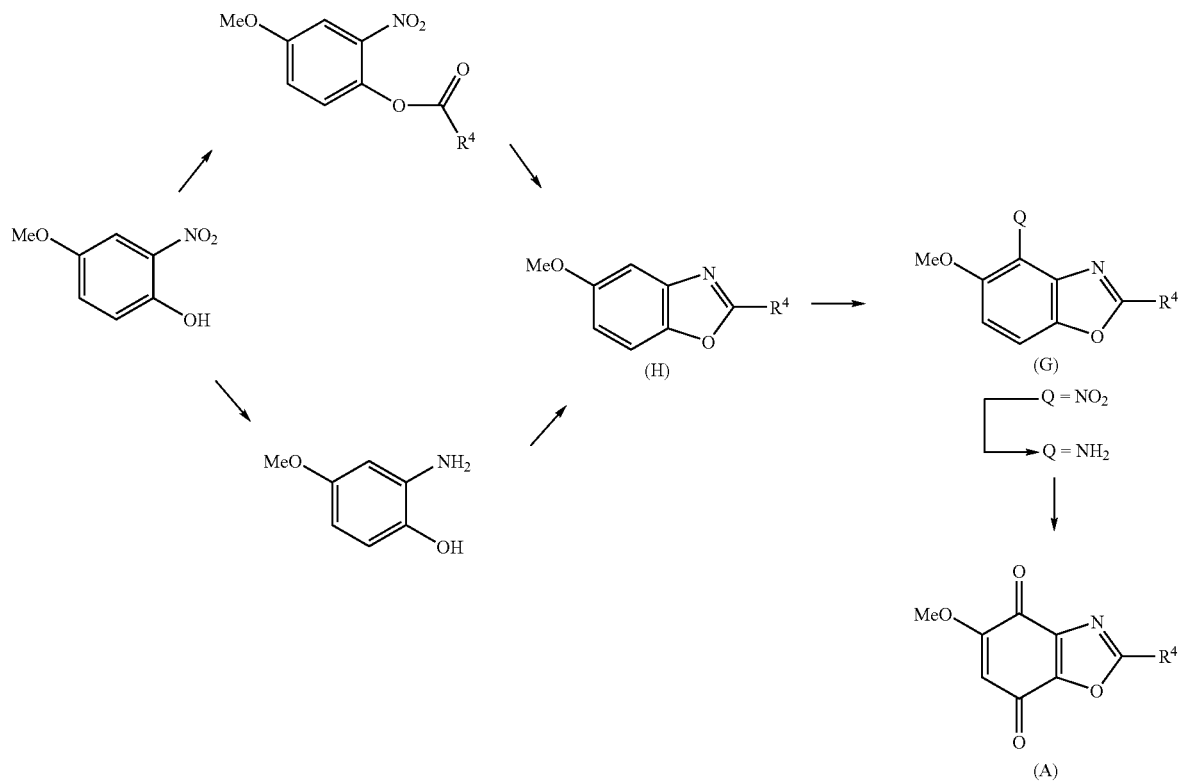

-continued

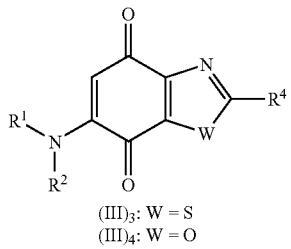

(III)₃: W = S
(III)₄: W = O

According to this method, the compounds of general formula (III)₃ or (III)₄, in which W, $R^1$, $R^2$ and $R^4$ are as defined above and $R^3$ represents H, are obtained by treatment of the compounds of general formula (K) with amines of general formula $R^1R^2NH$ in a protic solvent such as methanol or ethanol, at a temperature preferably comprised between 25° C. and the boiling temperature of the solvent (Yasuyuki Kita et al., *J. Org. Chem.* (1996), 61, 223-227).

In the case where it is also desired to substitute position 6 of the benzothiazoledione or benzoxazoledione nucleus (compounds of general formula (III)₃ or (III)₄ in which $R^3 \neq H$), it is sufficient to carry out an additional substitution using conditions familiar to a person skilled in the art.

i) W Represents a Sulphur Atom:

Preparation of the Intermediates of General Formula (K)

When W represents a sulphur atom, the intermediates of general formula (K) can be prepared according to the process represented in Diagram 6 hereafter.

Diagram 6

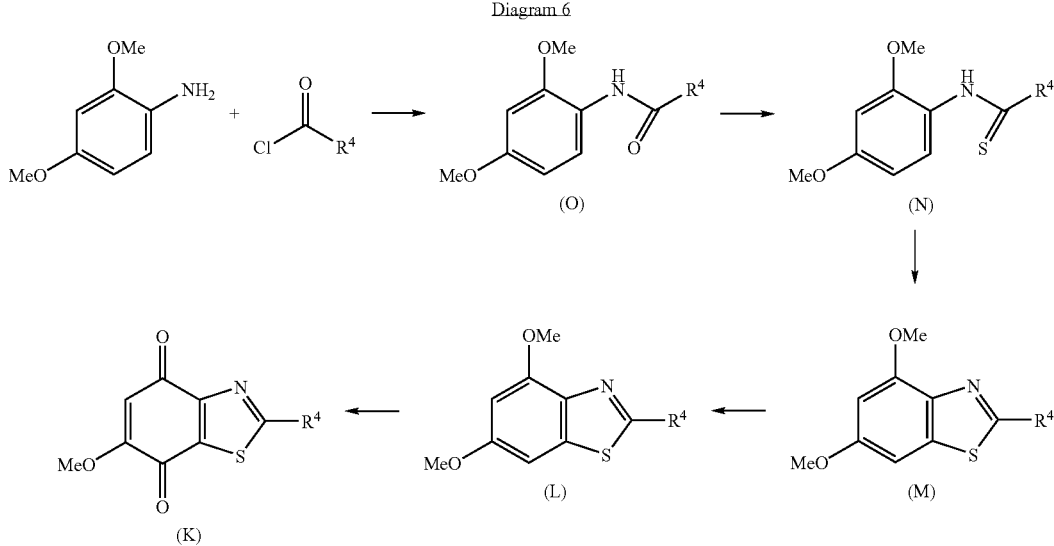

The compounds of general formula (K) in which $R^4$ is as defined above can be obtained according to a process analogous to that described for the preparation of the intermediates of general formula (A) (cf. Diagrams 2 and 3), the starting product being 2,4-dimethoxyaniline (commercial).

It is also possible to envisage the preparation of intermediates of general formula (K) in which W represents a sulphur atom according to the process described in Diagram 6a hereafter.

Diagram 6a

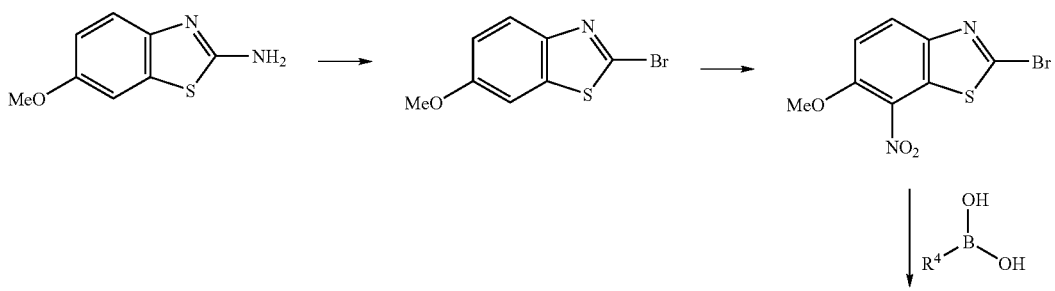

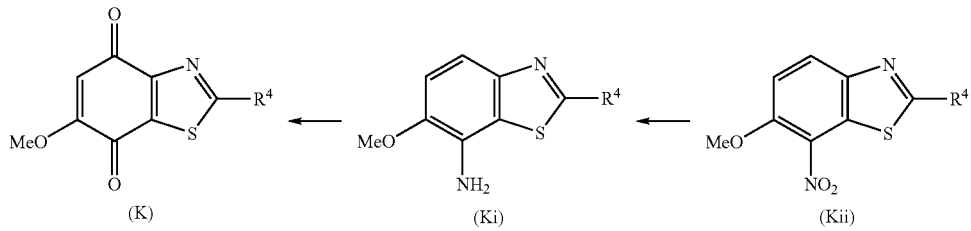

According to the alternative synthesis presented in Diagram 6a, 6-methoxy-1,3-benzothiazol-2-amine (commercial) is converted, according to Sandmeyer's method, known to a person skilled in the art, to 2-bromo-6-methoxy-1,3-benzothiazole, itself nitrated according to the methods known to a person skilled in the art in order to obtain 2-bromo-6-methoxy-7-nitro-1,3-benzothiazole. The intermediate of general formula (K.ii) is then obtained by condensation with boronic acids, according to Suzuki's method, known to a person skilled in the art. The intermediates of general formula (K) are obtained after reduction of the nitro group by the action of hydrogen in the presence of palladium on carbon or by the action of tin chloride in order to obtain the intermediate of general formula (K.i) which is then oxidized in order to obtain the quinone of general formula (K) by the action of Fremy's salt in acetone in the presence of a sodium hydrogen phosphate solution (G. R. Allen Jr et al., *J Med Chem* (1967), 10, 23).

ii) W Represents an Oxygen Atom:

Preparation of the Intermediates of General Formula (K)

When W represents an oxygen atom, the intermediates of general formula (K) can be prepared according to the process represented in Diagram 7 hereafter.

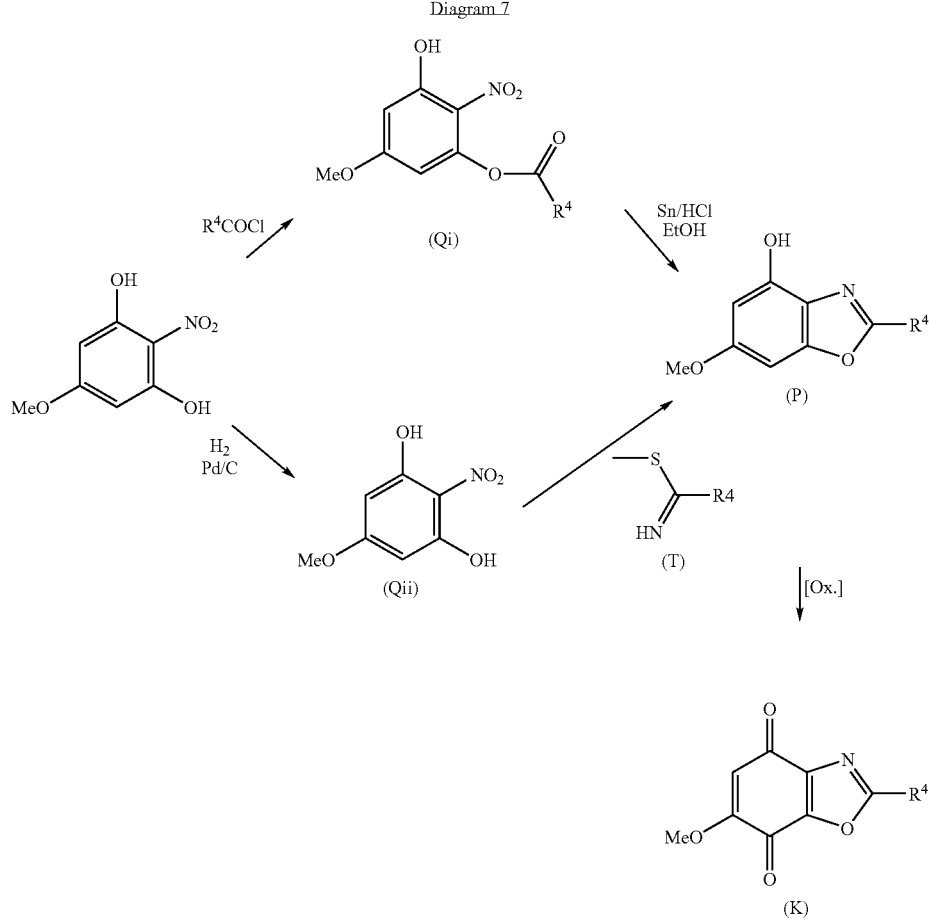

The methods presented in Diagram 7 are analogous to those presented in Diagram 4, but this time the starting product is 5-methoxy-2-nitro-resorcinol (described in particular by J. F. Grove et al. *J. Chem. Soc.* (1956), 1956-1963).

Alternatively, the method represented in Diagram 8 hereafter can also be used.

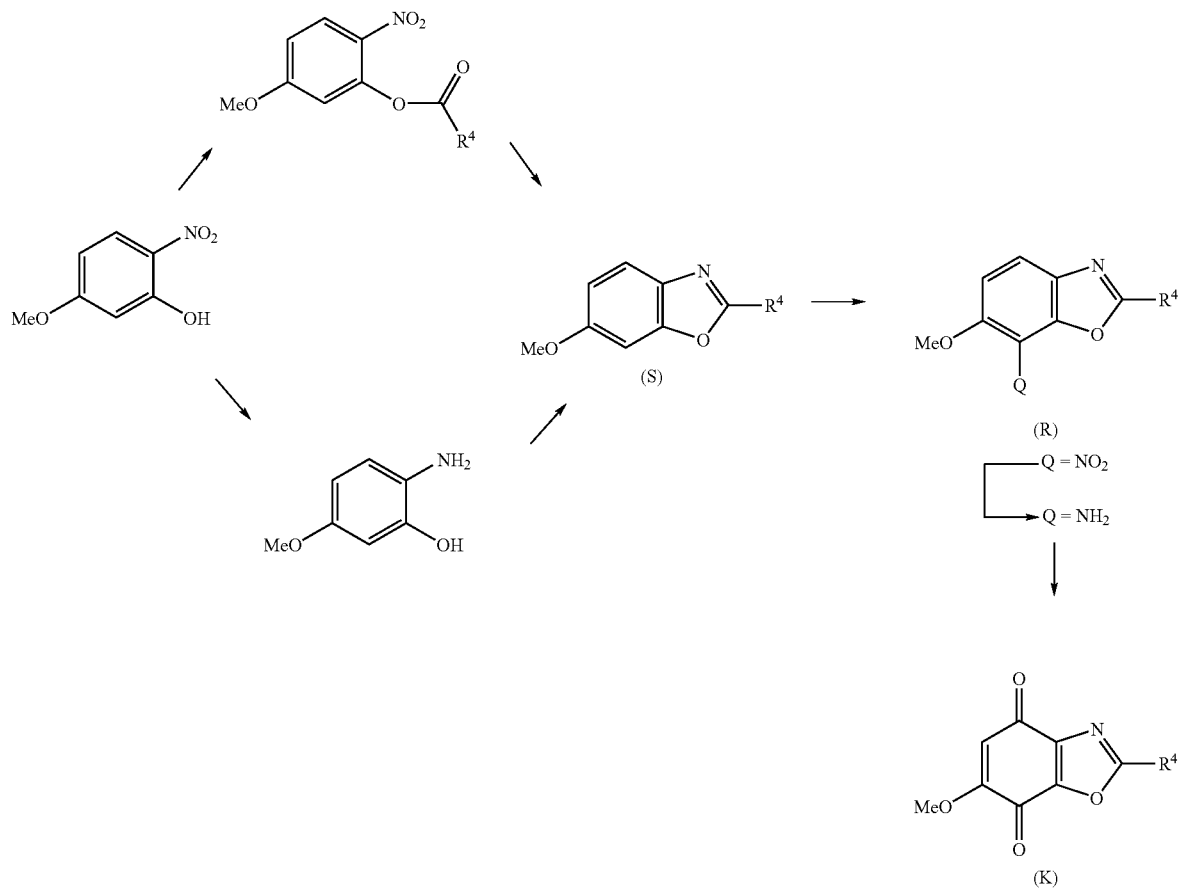

According to this method, (commercial) 5-methoxy-2-nitrophenol is converted to 6-methoxy-benzoxazole derivative of general formula (S), either using a dehydrating esterification/reduction reaction as presented in Diagram 4, or by reduction followed by condensation described previously. The intermediate of general formula (S) is then nitrated and reduced to the corresponding amine of general formula (R) according to the process presented in Diagram 3, then oxidized as previously to the quinone of general formula (K).

As regards the temperatures referred to in the present text, the term "approximately XX° C." indicates that the temperature in question corresponds to a range of more or less 10° C., either side of the temperature XX° C., and preferably to a range of more or less 5° C., either side of the temperature XX° C.

Unless otherwise specified, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as a limit to the scope of the invention.

EXAMPLES

Method Use for Measuring the Retention Time (r.t.) and the Molecular Peak (MH+)

The compounds are characterized by their retention time (r.t.), expressed in minutes, determined by liquid chromatography (LC), and their molecular peak (MH+) determined by mass spectrometry (MS), a single quadripole mass spectrometer (Micromass, Platform model) equipped with an electrospray source is used with a resolution of 0.8 Da at 50% valley.

For Examples 1 to 7 below, the elution conditions corresponding to the results indicated are the following: transition of an acetonitrile-water-trifluoroacetic acid mixture 50-950-0.2 (A) to an acetonitrile-water mixture 950-50 (B) via a linear gradient over a period of 8.5 minutes, then elution with the pure mixture B for 10.5 minutes. For Examples 8 to 60 hereafter, the elution conditions corresponding to the results indicated are the following: elution with an acetonitrile-water-acid trifluoroacetic mixture 50-950-0.2 (A) for 1 minute, then transition of mixture A to an acetonitrile-water mixture 950-50 (B) by a linear gradient over a period of 7.5 minutes, then elution with pure mixture B for 2 minutes.

Example 1

2-(2,6-difluorophenyl)-5-{[2-(dimethylamino)ethyl]amino}-1,3-benzothiazole-4,7-dione 1.1) N-(3,5-dimethoxyphenyl)-2,6-difluorobenzamide:

5.5 ml (39.2 mmol; 1.2 equivalent) of triethylamine and 4.5 ml (35.9 mmol; 1.1 equivalent) of 2,6-difluorobenzoyl chloride are added to 5 g (32.6 mmol) of 3,5-dimethoxyaniline in solution in 100 ml of anhydrous toluene. The reaction medium is maintained under stirring at 70° C. for 1 hour 30 minutes, then, after returning to ambient temperature, washed with 3 times 50 ml of water. The resulting organic phase is dried over magnesium sulphate then the solvent is evaporated off under reduced pressure. The expected product is obtained in the form of a white powder (8.75 g; yield=97%) used in the following stage without other purification.

MS-LC: MH+=294.11; r.t.=9.93 min.

1.2) N-(3,5-dimethoxyphenyl)-2,6-difluorobenzenecarbothioamide:

20.3 g (50 mmol; 1.5 equivalents) of Lawesson's reagent is added to 9.8 g (33.4 mmol) of N-(3,5-dimethoxyphenyl)-2,6-difluorobenzamide in solution in 150 ml of anhydrous toluene. The reaction medium is maintained under stirring at 120° C. for 8 hours, then, after returning to ambient temperature, is washed with 3 times 75 ml of water. The resulting organic phase is dried over magnesium sulphate then the solvent is evaporated off under reduced pressure. The residue is purified by chromatography on a silica column (eluent: dichloromethane/methanol 98/2) and the expected product is obtained in the form of a green oil (10 g; yield=96%).

MS-LC: MH+=310.06; r.t.=10.53 min.

1.3) 2-(2,6-difluorophenyl)-5,7-dimethoxy-1,3-benzothiazole:

170 ml (103 mmol; 3 equivalents) of a freshly prepared 20% aqueous solution of potassium ferricyanide is added to 10.3 g (33.3 mmol) of N-(3,5-dimethoxyphenyl)-2,6-difluorobenzenecarbothioamide dissolved in 150 ml of a 1.5M soda solution. The reaction medium is maintained under stirring at ambient temperature for 24 hours, then the beige precipitate formed is filtered, washed with water and dried (6.8 g; yield=66%). The mother liquors can be extracted by 3 times 75 ml of dichloromethane, then the organic phases are washed with a saturated solution of sodium chloride. After concentration under reduced pressure, the residue obtained can be purified on a silica column (eluent: ethyl acetate/heptane: 1/3) in order to provide another 2 g of expected product (overall yield=86%). Melting point: 136-138° C.

NMR $^1$H (DMSO d6, 400 MHz, δ): 7.65 (m, 1H, arom. H); 7.36-7.31 (m, 3H, arom. H); 6.75 (m, 1H, arom. H); 3.96 (s, 3H, $CH_3$); 3.87 (s, 3H, $CH_3$). MS-LC: MH+=308.12; r.t.=11.48 min.

1.4) 2-(2,6-difluorophenyl)-5-methoxy-1,3-benzothiazole-4,7-dione:

1.4.1) 2-(2,6-difluorophenyl)-5,7-dimethoxy-4-nitro-1,3-benzothiazole:

A solution of 16 g (29.3 mmol; 3 equivalents) of cerium ammonium nitrate in 40 ml of water is added dropwise to 3 g (9.76 mmol) of 2-(2,6-difluorophenyl)-5,7-dimethoxy-1,3-benzothiazole in solution in 75 ml of ethyl acetate. The reaction mixture is maintained under stirring for 2 hours at ambient temperature, then washed with 3 times 20 ml of water. The organic phases are dried over magnesium sulphate, filtered then concentrated under reduced pressure. The residue is purified by chromatography on a silica column (eluent: ethyl acetate/heptane: 3/7). Two fractions are separated:

0.3 g (yield=10%) of 2-(2,6-difluorophenyl)-5-methoxy-1,3-benzothiazole-4,7-dione is obtained in the form of yellow powder.

MS-LC: MH+=308.08; r.t.=10 min.

1.5 g of 2-(2,6-difluorophenyl)-5,7-dimethoxy-4-nitro-1,3-benzothiazole (45% yield) is obtained in the form of orange-coloured powder.

NMR $^1$H (DMSO d6, 400 MHz, δ): 7.72 (m, 1H, arom. H); 7.38 (m, 2H, arom. H); 7.11 (m, 1H, arom. H); 4.12 (s, 3H, $CH_3$); 4.07 (s, 3H, $CH_3$). MS-LC: MH+=353.05; r.t.=11.30 min.

1.4.2) 2-(2,6-difluorophenyl)-5,7-dimethoxy-1,3-benzothiazol-4-amine:

230 mg (0.65 mmol) of intermediate 1.4.1 dissolved in 15 ml of concentrated hydrochloric acid is reacted with 0.5 g (2.2 mmol; 3.4 equivalents) of dihydrated tin chloride in 5 ml of water. The reaction mixture is maintained under stirring for 2 hours at 50° C., then after returning to ambient temperature, poured on ice before being neutralized with a 5M soda solution. The product is then extracted with 3 times 15 ml of dichloromethane, the organic phases are combined, washed with a saturated solution of sodium chloride, dried over magnesium sulphate, filtered, then, after concentration under reduced pressure, the expected product is obtained in the form of a yellow oil. It is used in the following stage without other purification.

NMR $^1$H (DMSO d6, 400 MHz, δ): 7.67 (m, 1H, arom. H); 7.34 (m, 2H, arom. H); 6.92 (s, 1H, arom. H); 3.91 (s, 3H, $CH_3$); 3.90 (s, 3H, $CH_3$). MS-LC: MH+=323.10; r.t.=9.86 min.

1.4.3) 2-(2,6-difluorophenyl)-5-methoxy-1,3-benzothiazole-4,7-dione:

A solution of 1.22 g of cerium ammonium nitrate (2.23 mmol, 2.1 equivalents) in 8 ml of water is added to 343 mg (1.06 mmol) of 2-(2,6-difluorophenyl)-5,7-dimethoxy-1,3-benzothiazol-4-amine in solution in 25 ml of ethyl acetate. The reaction mixture is maintained under vigorous stirring at ambient temperature for 1 hour 30 minutes then the organic phase is separated and washed with 3 times 20 ml of water, then dried over magnesium sulphate, filtered and the solvent is evaporated off under reduced pressure. The residue is purified by chromatography on a silica column (eluent: ethyl acetate/heptane: 3/7) and 280 mg (yield=86%) of 2-(2,6-difluorophenyl)-5-methoxy-1,3-benzothiazole-4,7-dione is obtained in the form of yellow powder.

NMR $^1$H (DMSO d6, 400 MHz, δ): 7.72 (m, 1H, arom. H); 7.39 (m, 2H, arom. H); 6.32 (s, 1H, CH); 3.88 (s, 3H, $CH_3$). MS-LC: MH+=308.05; r.t.=9.99 min.

1.5) 2-(2,6-difluorophenyl)-5-{[2-(dimethylamino)ethyl]amino}-1,3-benzothiazole-4,7-dione:

104 ml (0.95 mmol; 1.5 equivalents) of N,N-dimethylethylenediamine are added to 195 mg of 2-(2,6-difluorophenyl)-5-methoxy-1,3-benzothiazole-4,7-dione in solution in 20 ml of anhydrous ethanol. The reaction mixture is stirred at 70° C. for 2 hours then the solvent is evaporated off under reduced pressure. The residue is purified on a silica column (eluent: 5% methanol in dichloromethane). 130 mg (yield=57%) of expected compound is obtained in the form of a red powder.

NMR $^1$H (DMSO d6, 400 MHz, δ): 7.72 (m, 1H, arom. H); 7.52 (m, 1H, NH.); 7.38 (m, 2H, arom. H); 5.60 (s, 1H, CH); 3.28 (m, 2H, CH$_2$); 2.53 (m, 2H, CH$_2$); 2.20 (s, 6H, 2CH$_3$). MS-LC: MH+=364.14; r.t.=7.85 min.

The compounds of Examples 2 to 7 are obtained in a similar manner to that described for Example 1, with appropriate acyl chlorides replacing 2,6-difluorobenzoyl chloride in the first stage and N-(2-aminoethyl)pyrrolidine replacing N,N-dimethylethylenediamine in the last stage for Examples 3, 5 and 7.

Example 2

2-(2,5-dichlorothien-3-yl)-5-{1-[2-(dimethylamino)ethyl]amino}-1,3-benzothiazole-4,7-dione:

2.1) 1,5-dichloro-N-(3,5-dimethoxyphenyl)thiophene-3-carboxamide:

NMR $^1$H (DMSO d6, 400 MHz, δ): 10.20 (s, 1H, NH); 7.47 (s, 1H, arom. H); 6.95 (s, 1H, arom. H); 6.27 (s, 1H, arom. H); 3.72 (s, 6H, 2CH$_3$). MS-LC: MH+=332.01; r.t.=11.08 min.

2.2) 2,5-dichloro-N-(3,5-dimethoxyphenyl)thiophene-3-carbothioamide:

NMR $^1$H (DMSO d6, 400 MHz, δ): 11.96 (s, 1H, NH); 7.30 (s, 1H, arom. H); 7.25 (s, 1H, arom. H); 6.44 (s, 1H, arom. H); 3.74 (s, 6H, 2CH$_3$). MS-LC: MH+=348.00; r.t.=11.55 min.

2.3) 2-(2,5-dichlorothien-3-yl)-5,7-dimethoxy-1,3-benzothiazole:

NMR $^1$H (DMSO d6, 400 MHz, δ): 7.72 (s, 1H, arom. H); 7.22 (s, 1H, arom. H); 6.73 (s, 1H, arom. H); 3.96 (s, 3H, CH$_3$); 3.86 (s, 3H, CH$_3$). MS-LC: MH+=345.94; r.t.=12.77 min.

2.4) 2-(2,5-dichlorothien-3-yl)-5-methoxy-1,3-benzothiazole-4,7-dione:

NMR $^1$H (DMSO d6, 400 MHz, δ): 7.75 (s, 1H, arom. H); 6.31 (s, 1H, CH); 3.88 (s, 3H, CH$_3$). MS-LC: MH+=345.98; r.t.=11.52 min.

2.5) 2-(2,5-dichlorothien-3-yl)-5-{[2-(dimethylamino)ethyl]amino}-1,3-benzothiazole-4,7-dione:

NMR $^1$H (DMSO d6, 400 MHz, δ): 7.72 (s, 1H, arom. H); 7.51 (m, 1H, NH.); 5.58 (s, 1H, CH); 3.36 (m, 2H, CH$_2$); 2.54 (m, 2H, CH$_2$); 2.20 (s, 6H, 2CH$_3$).

MS-LC: MH+=402.06; r.t.=8.42 min.

Example 3

2-(2,5-dichlorothien-3-yl)-5-[(2-pyrrolidin-1-ylethyl)amino]-1,3-benzothiazole-4,7-dione:

MS-LC: MH+=427.97; r.t.=8.70 min.

Example 4

5-{[2-(dimethylamino)ethyl]amino}-2-(4-fluorophenyl)-1,3-benzothiazole4,7-dione 4.1) N-(3,5-dimethoxyphenyl)-4-fluorobenzamide:

NMR $^1$H (DMSO d6, 400 MHz, δ): 10.15 (s, 1H, NH); 8.01 (m, 2H, arom. H); 7.36 (m, 2H, arom. H); 7.05 (m, 2H, arom. H); 6.26 (s, 1H, arom. H); 3.73 (s, 6H, 2CH$_3$). MS-LC: MH+=276.17; r.t.=10.07 min.

4.2) N-(3,5-dimethoxyphenyl)-4-fluorobenzenecarbothioamide:

MS-LC: MH+=292.17; r.t.=10.72 min.

4.3) 2-(4-fluorophenyl)-5, 7-dimethoxy-1,3-benzothiazole:

NMR $^1$H (DMSO d6, 400 MHz, δ): 8.11 (m, 2H, arom. H); 7.40 (m, 2H, arom. H); 7.22 (s, 1H, arom. H); 6.69 (s, 1H, arom. H); 3.95 (s, 3H, CH$_3$); 3.86 (s, 3H, CH$_3$). MS-LC: MH+=290.07; r.t.=11.93 min.

4.4) 2-(4-fluorophenyl)-5-methoxy-1,3-benzothiazole-4,7-dione

NMR $^1$H (DMSO d6, 400 MHz, δ): 8.15 (m, 2H, arom. H); 7.42 (m, 2H, arom. H); 6.28 (s, 1H, CH); 3.87 (s, 3H, CH$_3$). MS-LC: MH+=290.14; r.t.=11.95 min.

4.5) 5-{[2-(dimethylamino)ethyl]amino}-2-(4-fluorophenyl)-1,3-benzothiazole-4,7-dione NMR $^1$H (DMSO d6, 400 MHz, δ): 8.11 (m, 2H, arom. H); 7.48 (m, 1H, NH); 7.41 (m, 2H, arom. H); 5.57 (s, 1H, CH); 3.26 (m, 2H, CH$_2$); 2.55 (m, 2H, CH$_2$); 2.22 (s, 6H, 2CH$_3$). MS-LC: MH+=346.18; r.t.=8.01 min.

Example 5

2-(4-fluorophenyl)-5-[(2-pyrrolidin-1-ylethyl)amino]-1,3-benzothiazole-4,7-dione NMR $^1$H (DMSO d6, 400 MHz, δ): 8.12 (m, 2H, arom. H); 7.58 (m, 1H, NH); 7.41 (m, 2H, arom. H); 5.55 (s, 1H, CH); 3.41 (m, 2H, CH$_2$); 2.69 (m, 2H, CH$_2$); 2.51 (m, 2H, CH$_2$); 2.44 (m, 2H, CH2); 1.70 (m, 4H, 2CH2). MS-LC: MH+=372.19; r.t.=8.12 min.

Example 6

2-(2-chloro-6-fluorophenyl)-5-{[2-(dimethylamino)ethyl]amino}-1,3-benzothiazole4,7-dione 6.1) 2-chloro-N-(3,5-dimethoxyphenyl)-6-fluorobenzamide:

NMR $^1$H (DMSO d6, 400 MHz, δ): 10.69 (s, 1H, NH); 7.53 (m, 1H, arom. H); 7.43 (m, 1H, arom. H); 7.37 (m, 1H, arom. H); 6.93 (m, 2H, arom. H); 6.29 (s, 1H, arom. H); 3.72 (s, 6H, 2CH$_3$). MS-LC: MH+=310.15; r.t.=10.11 min.

6.2) 2-chloro-N-(3,5-dimethoxyphenyl)-6-fluorobenzenecarbothioamide:

NMR $^1$H (DMSO d6, 400 MHz, δ): 7.41 (m, 2H, arom. H); 7.27 (m, 3H, arom. H); 6.46 (s, 1H, arom. H); 3.75 (s, 6H, 2CH$_3$). MS-LC: MH+=326.09; r.t.=10.73 min.

6.3) 2-(2-chloro-6-fluorophenyl)-5, 7-dimethoxy-1,3-benzothiazole:

NMR $^1$H (DMSO d6, 400 MHz, δ): 7.66 (m, 1H, arom. H); 7.56 (m, 1H, arom. H); 7.47 (m, 1H, arom. H); 7.30 (s, 1H, arom. H); 6.77 (s, 1H, arom. H); 3.96 (s, 3H, CH$_3$); 3.88 (s, 3H, CH$_3$). MS-LC: MH+=324.03; r.t.=11.60 min.

6.4) 2-(2-chloro-6-fluorophenyl)-5-methoxy-1,3-benzothiazole-4,7-dione

NMR $^1$H (DMSO d6, 400 MHz, δ): 7.69 (m, 1H, arom. H); 7.61 (m, 1H, arom. H); 7.52 (m, 1H, arom. H); 6.32 (s, 1H, CH); 3.88 (s, 3H, $CH_3$). MS-LC: MH+=324.03; r.t.=9.23 min.

6.5) 2-(2-chloro-6-fluorophenyl)-5-{[2-(dimethylamino) ethyl]amino}-1,3-benzothiazole-4,7-dione NMR $^1$H (DMSO d6, 400 MHz, δ): 7.67 (s, 1H, arom. H); 7.59 (m, 1H, arom. H); 7.55 (m, 1H, NH.); 7.49 (m, 1H, arom. H); 5.61 (s, 1H, CH); 3.36 (m, 2H, $CH_2$); 2.54 (m, 2H, $CH_2$); 2.19 (s, 6H, $2CH_3$). MS-LC: MH+=380.10; r.t.=7.88 min.

Example 7

2-(2-chloro-6-fluorophenyl)-5-[(2-pyrrolidin-1-yl-ethyl)amino]-1,3-benzothiazole-4,7-dione MS-LC: MH+=406.10; r.t.=8.01 min.

Example 8

6-{[2-(dimethylamino)ethyl]amino}-2-(4-fluorophenyl)-1,3-benzothiazole4,7-dione 8.1) N-(2,4-dimethoxyphenyl)-4-fluorobenzamide:

The protocol is identical to that described for Example 1.1, with 4-fluorobenzoyl chloride replacing 2,6-difluorobenzoyl chloride and 2,4-dimethoxyaniline replacing 3,5-dimethoxyaniline.

MS-LC: MH+=276.14; r.t.=10.11 min.

8.2) N-(2,4-dimethoxyphenyl)-4-fluorobenzenecarbothioamide:

11 g (131 mmol; 4 equivalents) of $NaHCO_3$ is added to 9 g (32.7 mmol) of N-(2,4-dimethoxyphenyl)-4-fluorobenzamide dissolved in 350 ml of 1,2-dimethoxyethane. 29 g (65.2 mmol; 2 equivalents) of phosphorus pentasulphide ($P_2S_5$) is then added by parts to the reaction medium which is maintained under stirring under an inert atmosphere of argon at 85° C. for 4 hours. 250 ml of a saturated solution of $NaHCO_3$ are then added to the medium then the product is extracted with 3 times 200 ml of ethyl acetate. The combined organic phases are washed with twice 200 ml of a saturated solution of NaCl, then dried over sodium sulphate. The solvents are evaporated off under reduced pressure and the residue purified on a silica column (eluent: ethyl acetate/heptane mixture 1:4) in order to provide 4.65 g (yield=49%) of expected product.

MS-LC: MH+=292.11; r.t.=10.70 min.

8.3) 2-(4-fluorophenyl)-4,6-dimethoxy-1,3-benzothiazole:

The protocol is identical to that described for Stage 1.3 of Example 1, with N-(2,4-dimethoxyphenyl)-4-fluorobenzenecarbothioamide replacing N-(3,5-dimethoxyphenyl)-2,6-difluorobenzenecarbothioamide.

MS-LC: MH+=290.12; r.t.=11.51 min.

8.4) 2-(4-fluorophenyl)-6-methoxy-1,3-benzothiazole-4,7-dione 63 ml of a freshly prepared 0.65 M cerium ammonium nitrate solution is added, dropwise, to 3.8 g (13.1 mmol) of 2-(4-fluorophenyl)-4,6-dimethoxy-1,3-benzothiazole in solution in 100 ml of ethyl acetate. The reaction mixture is maintained under stirring at ambient temperature for 3 hours then the aqueous phase is separated and washed with 3 times 75 ml of ethyl acetate. The organic phases are combined, dried over sodium sulphate and the solvents are evaporated off under reduced pressure. The residue is purified by chromatography on a silica column (eluent: ethyl acetate/ heptane mixture 1:3) in order to provide 0.6 g (16% yield) of expected product.

MS-LC: MH+=290.05; r.t.=10.30 min.

8.5) 6-{[2-(dimethylamino)ethyl]amino}-2-(4-fluorophenyl)-1,3-benzothiazole-4,7-dione The protocol is identical to that described for Stage 1.5 of Example 1, with 2-(4-fluorophenyl)-6-methoxy-1,3-benzothiazole-4,7-dione replacing 2-(2,6-difluorophenyl)-5-methoxy-1,3-benzothiazole-4,7-dione. The expected compound is obtained in the form of a red powder.

Melting point: 246-247° C. NMR $^1$H (DMSO d6, 400 MHz, δ): 8.14-8.18 (m, 2H, arom. H); 7.40-7.45 (m, 2H, arom. H); 7.30 (t, 1H, NH.); 5.50 (s, 1H, CH); 3.26 (m, 2H, $CH_2$); 2.50 (m, 2H, $CH_2$); 2.20 (s, 6H, $2CH_3$). MS-LC: MH+=346.14; r.t.=8.21 min.

The compounds of Examples 9 to 12 are obtained in a similar manner to that described for Example 8, with appropriate acyl chlorides replacing 4-fluorobenzoyl chloride in the first stage.

Example 9

6-{[2-(dimethylamino)ethyl]amino}-2-(1-naphthyl)-1,3-benzothiazole-4,7-dione

The expected compound is obtained in the form of a brown powder. Melting point: 172-173° C.

MS-LC: MH+=378.14; r.t.=8.52 min.

Example 10

2-(1,1'-biphenyl-4-yl)-6-{[2-(dimethylamino)ethyl] amino}-1,3-benzothiazole-4,7-dione The expected compound is obtained in the form of a red powder. Melting point: 194-195° C.

MS-LC: MH+=404.13; r.t.=9.07 min.

Example 11

2-(4-butylphenyl)-6-{[2-(dimethylamino)ethyl] amino}-1,3-benzothiazole-4,7-dione The expected compound is obtained in the form of a brown powder. Melting point: 126-127° C.

MS-LC: MH+=384.19; r.t.=9.35 min.

Example 12

2-(2-chloro-6fluorophenyl)-6-{[2-(dimethylamino) ethyl]amino}-1,3-benzothiazole-4,7-dione The expected compound is obtained in the form of a red powder.

MS-LC: MH+=380.06; r.t.=7.89 min.

Example 13

6-{[2-(dimethylamino)ethyl]amino}-2-(2-naphthyl)-1,3-benzothiazole-4,7-dione 13.1) 2-bromo-6-methoxy-1,3-benzothiazol-2-amine:

20 g (111 mmol) of 6-methoxy-1,3-benzothiazol-2-amine is solubilized in 400 ml of acetonitrile, then 13.2 ml (111 mmol; 1 equivalent) of tert-butyl nitrite and 29 g (130 mmol;

1.2 equivalent) of CuBr$_2$ are added to the reaction medium which is then maintained under stirring at 80° C. for 2 hours. The solvent is evaporated off under reduced pressure, then the residue is taken up in 250 ml of ethyl acetate and washed twice with 200 ml of water. The organic phase is dried over sodium sulphate, then the solvent is evaporated off under reduced pressure and 24 g (yield=89%) of 2-bromo-6-methoxy-1,3-benzothiazol-2-amine is obtained and used without other purification in the following stage.

MS-LC: MH+=243.98; r.t.=10.89 min.

13.2) 2-bromo-6-methoxy-7-nitro-1,3-benzothiazole:

24 g (100 mmol) of 2-bromo-6-methoxy-1,3-benzothiazol-2-amine is dissolved in 30 ml of sulphuric acid at 0° C., then 30 ml of nitric acid (density 1.41) is added dropwise.

Stirring is maintained for 30 minutes at 0° C. then for 1 hour at ambient temperature. After neutralization of the reaction mixture by a 35% soda solution (13.5M), the product formed is extracted with 3 times 100 ml of dichloromethane. The organic phase is dried over sodium sulphate then the solvent is evaporated off under reduced pressure and the solid thus obtained is taken up in dichloromethane, filtered and washed with a dichloromethane/heptane mixture 1:1. The mother liquors are purified by chromatography on a silica column (eluent: ethyl acetate/heptane mixture 1:1). 9.9 g (yield=35%) of 2-bromo-6-methoxy-7-nitro-1,3-benzothiazole is obtained in the form of orange-coloured powder.

MS-LC: MH+=288.75; r.t.=10.70 min.

13.3) 6-methoxy-2-(2-naphthyl)-7-nitro-1,3-benzothiazole:

0.716 g (4.16 mmol; 1.1 equivalent) of 2-naphthalene boronic acid as well as a solution of 1.2 g (11.35 mmol; 3 equivalents) of sodium carbonate in 15 ml of water are added to a suspension of 1.09 g (3.78 mmol) of 2-bromo-6-methoxy-7-nitro-1,3-benzothiazole and 131 mg (0.114 mmol; 0.03 equivalent) of palladium tetrakis-triphenylphosphine in 30 ml of 1,2-dimethoxyethane. The reaction mixture is maintained under stirring at 85.5° C. for 18 hours, then after concentration under reduced pressure, 100 ml of ethyl acetate is added to the medium which is then washed with twice 75 ml of a saturated aqueous solution of sodium chloride. The organic phase is dried over sodium sulphate then the solvents are evaporated off under reduced pressure and the residue is purified by chromatography on a silica column (eluent: ethyl acetate/heptane mixture 1:2). 1.06 g (83% yield) of 6-methoxy-2-(2-naphthyl)-7-nitro-1,3-benzothiazole is obtained in the form of beige powder.

MS-LC: MH+=337.14; r.t.=12.54 min.

13.4) 6-methoxy-2-(2-naphthyl)-1,3-benzothiazol-7-amine:

1.06 g (3.15 mmol) of 6-methoxy-2-(2-naphthyl)-7-nitro-1,3-benzothiazole are put into suspension in 50 ml of methanol and 5 ml of acetic acid. 105 mg (10%) of palladium on carbon is added to the reaction mixture which is maintained under stirring under 2.5 bars of hydrogen for 24 hours. The catalyst is filtered, then the solvents are evaporated under reduced pressure. 0.51 g (yield=53%) of 6-methoxy-2-(2-naphthyl)-1,3-benzothiazol-7-amine is obtained and used in the following stage without other purification.

MS-LC: MH+=307.14; r.t.=11.57 min.

13.5) 6-methoxy-2-(2-naphthyl)-1,3-benzothiazol-4,7-dione 0.8 g (3 mmol; 1.8 equivalent) of Fremy's salt dissolved in 45 ml of 0.3 M of sodium hydrogen phosphate solution is added to 0.51 g (1.67 mmol) of 6-methoxy-2-(2-naphthyl)-1,3-benzothiazol-7-amine in solution in 20 ml of acetone. The reaction mixture is maintained under stirring at ambient temperature for 18 hours then concentrated under reduced pressure. The product formed is extracted with 3 times 50 ml of dichloromethane and the aqueous phase is washed with 50 ml of a saturated aqueous solution of sodium chloride. The organic phases are combined, dried over sodium sulphate and the solvent is evaporated off under reduced pressure. 0.5 g (yield=93%) of 6-methoxy-2-(2-naphthyl)-1,3-benzothiazol-4,7-dione is obtained and used in the following stage without other purification.

MS-LC: MH+=322.08; r.t.=11.26 min.

13.6) 6-{[2-(dimethylamino)ethyl]amino}-2-(2-naphthyl)-1,3-benzothiazol-4,7-dione The protocol is identical to that described for Stage 1.5 of Example 1, with 6-methoxy-2-(2-naphthyl)-1,3-benzothiazol-4,7-dione replacing 2-(2,6-difluorophenyl)-5-methoxy-1,3-benzothiazol-4,7-dione. The expected compound is obtained in the form of a red powder. Melting point: 167-168° C.

NMR $^1$H (DMSO d6, 400 MHz, δ): 8.76 (s, 1H, arom. H); 8.09-8.16 (m, 3H, arom. H); 8.00-8.03 (m, 1H, arom. H); 7.61-7.68 (m, 2H, arom. H); 7.30 (t, 1H, NH.); 5.52 (s, 1H, CH); 3.26 (m, 2H, CH$_2$); 2.50 (m, 2H, CH$_2$); 2.20 (s, 6H, 2CH$_3$). MS-LC: MH+=378.19; r.t.=8.34 min.

The compound of Example 14 is obtained in a similar manner to that described for Example 13, with 2,5-difluorophenylboronic acid replacing 2-naphthalene boronic acid in the third stage.

Example 14

2-(2,5-difluorophenyl)-6-{[2-(dimethylamino)ethyl] amino}-1,3-benzothiazole-4,7-dione The expected compound is obtained in the form of a red powder.

MS-LC: MH+=364.18; r.t.=8.03 min.

Example 15

2-(2,5-difluorophenyl)-5-{[2-(dimethylamino)ethyl] amino}-1,3-benzoxazole-4,7-dione 15.1) 2,5-difluorobenzenecarbothioamide:

10 g (71.9 mmol) of 2,5-difluorobenzonitrile and 16.2 g (215.7 mmol; 3 equivalents) of thioacetamide are dissolved in 80 ml of dimethylformamide containing 10% hydrochloric acid. The reaction mixture is maintained under stirring at 100° C. for 48 hours. After returning to ambient temperature, the reaction mixture is poured onto ice and insoluble material is filtered out. The mother liquors are extracted with 3 times 80 ml of ethyl acetate and the organic phases are washed with twice 50 ml of water. The organic phases are combined, dried over sodium sulphate and the solvents are evaporated under reduced pressure. The residue is purified by chromatography on a silica column (eluent: ethyl acetate/ heptane mixture 1:2) and 10.8 g (yield=87%) of 2,5-difluorobenzenecarbothioamide is obtained.

MS-LC: MH+=174.04; r.t.=8.94 min.

15.2) Methyl 2,5-difluorobenzenecarbimidothioate hydroiodide:

5.9 ml (94.2 mmol; 1.5 equivalents) of methyl iodide is added to 10.8 g (62 mmol) of 2,5-difluorobenzenecarbothioamide in solution in 70 ml of acetone. The reaction mixture is maintained under stirring at 25° C. for 24 hours, then the solvent is evaporated off under reduced pressure. Methyl 2,5-difluorobenzene carbimidothioate hydroiodide is obtained (18.4 g; yield=93%), after crystallization from ethyl ether, in the form of beige powder.

MS-LC: MH+=188.03; r.t.=7.27 min.

15.3) 2-(2,5-difluorophenyl)-5-methoxy-1,3-benzoxazol-7-amine:

7.1 g (33.3 mmol) of 4-methoxy-2,6-dinitrophenol (obtained according to the method described by P. Cotelle and J.-P. Catteau, *Synth. Commun.*, 26, (1996), 4105-4112) is dissolved in 100 ml of ethanol. 710 mg (10%) of palladium on carbon is added to the reaction mixture which is then stirred under a hydrogen atmosphere for 20 hours. Then the hydrogen is driven off using a stream of argon and a solution of 7 g (22.2 mmol; 0.67 equivalents) of methyl 2,5-difluorobenzene carbimidothioate hydroiodide in 60 ml of ethanol is added dropwise to the preceding mixture. The reaction is maintained under stirring at 25° C. for 24 hours, then the palladium is filtered out, the solvents are evaporated off under reduced pressure and the residue is purified by chromatography on a silica column (eluent: ethyl acetate/heptane mixture 1:2). 3.2 g (52% yield) of 2-(2,5-difluorophenyl)-5-methoxy-1,3-benzoxazol-7-amine is thus obtained in the form of beige powder.

MS-LC: MH+=277.17; r.t.=10.07 min.

15.4) 2-(2,5-difluorophenyl)-5-methoxy-1,3-benzoxazole-4,7-dione 7 g (16.2 mmol; 2.2 equivalents) of bis(trifluoroacetoxy)iodobenzene dissolved in 130 ml of an acetonitrile/water mixture 4/1 is added dropwise to a solution of 2.04 g (7.38 mmol) of 2-(2,5-difluorophenyl)-5-methoxy-1,3-benzoxazol-7-amine in 75 ml of an acetonitrile/water mixture 4:1 at −5° C. After stirring for 1 hour at −5° C., 150 ml of water is added to the reaction medium and the product formed is extracted with twice 300 ml of dichloromethane. The organic phases are combined and dried over sodium sulphate, then the solvents are evaporated off under reduced pressure. The residue is then purified by chromatography on a silica column (eluent: dichloromethane/methanol mixture 98:2) and 200 mg (10% yield) of 2-(2,5-difluorophenyl)-5-methoxy-1,3-benzoxazole-4,7-dione is obtained in the form of a yellow powder.

MS-LC: MH+=292.07; r.t.=9.98 min.

15.5) 2-(2,5-difluorophenyl)-5-{[2-(dimethylamino)ethyl]amino}-1,3-benzoxazole-4,7-dione The protocol is identical to that described for Example 1.5, with 2-(2,5-difluorophenyl)-5-methoxy-1,3-benzoxazole-4,7-dione replacing 2-(2,6-difluorophenyl)-5-methoxy-1,3-benzothiazol-4,7-dione. The expected compound is obtained in the form of a black powder. Melting point: 181-182° C.

NMR $^1$H (DMSO d6, 400 MHz, δ): 7.87-7.91 (m, 1H, arom. H); 7.56-7.60 (m, 3H, NH, arom. H); 5.43 (s, 1H, CH); 3.26 (m, 2H, CH$_2$); 2.50 (m, 2H, CH$_2$); 2.18 (s, 6H, 2CH$_3$). MS-LC: MH+=348.24; r.t.=7.80 min.

The compounds of Examples 16 to 23 are obtained in a similar manner to that described for Example 15, with suitable methyl carbimidothioate replacing methyl 2,5-difluorobenzenecarbimidothioate hydroiodide in the third stage.

Example 16

2-(2-bromophenyl)-5-{[2-(dimethylamino)ethyl]amino}-1,3-benzoxazole4,7-dione

The expected compound is obtained in the form of a red powder. Melting point: 153-154° C.

MS-LC: MH+=390.02; r.t.=7.93 min.

Example 17

2-(3-bromophenyl)-5-{[2-(dimethylamino)ethyl]amino}-1,3-benzoxazole-4,7-dione

The expected compound is obtained in the form of a red powder. Melting point: 187-188° C.

MS-LC: MH+=390.06; r.t.=8.03 min.

Example 18

5-{[2-(dimethylamino)ethyl]amino}-2-(4-fluorophenyl)-1,3-benzoxazole-4,7-dione

The expected compound is obtained in the form of a red powder. Melting point: 181-182° C.

MS-LC: MH+=330.18; r.t.=7.20 min.

Example 19

2-(3,5-difluorophenyl)-5-{[2-(dimethylamino)ethyl]amino}-1,3-benzoxazole-4,7-dione The expected compound is obtained in the form of a red powder.

Melting point: 187-188° C. MS-LC: MH+=348.14; r.t.=7.86 min.

Example 20

2-(2,3-difluorophenyl)-5-{[2-(dimethylamino)ethyl]amino}-1,3-benzoxazole-4,7-dione The expected compound is obtained in the form of a red powder. Melting point: 178-179° C.

MS-LC: MH+=348.30; r.t.=7.84 min.

Example 21

5-{[2-(dimethylamino)ethyl]amino}-2-(3,4,5-trifluorophenyl)-1,3-benzoxazole4,7-dione The expected compound is obtained in the form of a black powder. Melting point: 200-201° C.

MS-LC: MH+=266.27; r.t.=8.10 min.

Example 22

5-{[2-(dimethylamino)ethyl]amino}-2-(4-ethylphenyl)-1,3-benzoxazole4,7-dione

The expected compound is obtained in the form of a red powder. Melting point: 169-170° C.

MS-LC: MH+=340.23; r.t.=8.20 min.

Example 23

2-benzyl-5-{[2-(dimethylamino)ethyl]amino}-1,3-benzoxazole-4,7-dione

The expected compound is obtained in the form of a red powder. Melting point: 135-136° C.

MS-LC: MH+=326.22; r.t.=7.82 min.

The compounds of Examples 24 to 26 are obtained in a similar manner to that described for Example 15, with suitable methyl carbimidothioate replacing methyl 2,5-difluorobenzenecarbimidothioate hydroiodide in the third stage

Example 24

2-(3-bromophenyl)-5-[(2-pyrrolidin-1-ylethyl)amino]1,3-benzoxazole4,7-dione

The expected compound is obtained in the form of a black powder. Melting point: 169-170° C.
MS-LC: MH+=416.05; r.t.=8.61 min.

Example 25

2-(3,5-difluorophenyl)-5-[(2-pyrrolidin-1-ylethyl)amino]-1,3-benzoxazole-4,7-dione The expected compound is obtained in the form of a red powder. Melting point: 182-183° C.
MS-LC: MH+=374.12; r.t.=8.03 min.

Example 26

5-[(2-pyrrolidin-1-ylethyl)amino]-2-(3,4,5-trifluorophenyl)-1,3-benzoxazole-4,7-dione The expected compound is obtained in the form of a black powder. Melting point: 193-194° C.
MS-LC: MH+=392.27; r.t.=8.21 min.

Example 27

2-(2,5-difluorophenyl)-6-{[2-(dimethylamino)ethyl]amino}-1,3-benzoxazole-4,7-dione 27.1) 2-amino-5-methoxybenzene-1,3-diol:

3.36 g (18.1 mmol) of 5-methoxy-2-nitrobenzene-1,3-diol (obtained according to the protocol described by J. F. Grove et al., *J. Chem. Soc.* (1956), 1956-1963), is dissolved in 50 ml of ethanol. 336 mg of palladium (10%) on carbon is added to the reaction mixture which is then stirred under a hydrogen atmosphere for 20 hours. The palladium is filtered out and the solvent is evaporated off under reduced pressure. 2-amino-5-methoxybenzene-1,3-diol is used in the following stage without other purification.

27.2) 2-(2,5-difluorophenyl)-6-methoxy-1,3-benzoxazol-4-ol:

2.8 g (9.02 mmol; 1 equivalent) of methyl 2,5-difluorobenzene carbimidothioate hydroiodide in solution in 20 ml of ethanol is added to a solution of 1.4 g (9.02 mmol) of 2-amino-5-methoxybenzene-1,3-diol in 80 ml of ethanol. The reaction mixture is maintained under stirring at 78° C. for 5 hours then the solvent is evaporated off under reduced pressure. The residue is purified by chromatography on a silica column (eluent: dichloromethane/methanol mixture 98:2) and 860 mg (34% yield) of 2-(2,5-difluorophenyl)-6-methoxy-1,3-benzoxazol-4-ol is obtained.
MS-LC: MH+=278.15; r.t.=10.49 min.

27.3) 2-(2,5-difluorophenyl)-6-methoxy-1,3-benzoxazole-4,7-dione 2.9 g (6.81 mmol; 2.2 equivalents) of bis(trifluoroacetoxy)iodo benzene dissolved in 75 ml of an acetonitrile/water mixture 4:1 is added dropwise to a solution of 0.86 g (3.10 mmol) of 2-(2,5-difluorophenyl)-6-methoxy-1,3-benzoxazol-7-amine in 30 ml of an acetonitrile/water mixture 4:1 at −5° C. After stirring for 30 minutes at −5° C., 70 ml of water is added to the reaction medium and the product formed is extracted twice with 100 ml of dichloromethane. The organic phases are combined and dried over sodium sulphate, then the solvents are evaporated off under reduced pressure. The residue is then purified by chromatography on a silica column (eluent: dichloromethane/methanol mixture 99:1) and 475 mg (yield=53%) of 2-(2,5-difluorophenyl)-6-methoxy-1,3-benzoxazole-4,7-dione is obtained in the form of a yellow powder.
MS-LC: MH+=292.10; r.t.=9.97 min.

27.4) 2-(2,5-difluorophenyl)-6-{[2-(dimethylamino)ethyl]amino}-1,3-benzoxazole-4,7-dione The protocol is identical to that described for Stage 1.5 of Example 1, with 2-(2,5-difluorophenyl)-6-methoxy-1,3-benzoxazole-4,7-dione replacing 2-(2,6-difluorophenyl)-5-methoxy-1,3-benzothiazol-4,7-dione. The expected compound is obtained in the form of a black powder. Melting point: 162-163° C.
NMR $^1$H (DMSO d6, 400 MHz, δ): 7.91-7.95 (m, 1H, arom. H); 7.58-7.62 (m, 2H, arom. H); 7.38 (t, 1H, NH); 5.40 (s, 1H, CH); 3.23 (m, 2H, $CH_2$); 2.49 (m, 2H, $CH_2$); 2.18 (s, 6H, $2CH_3$). MS-LC: MH+=348.26; r.t.=7.80 min.

The compounds of Examples 28 to 44 are obtained in a similar manner to that described for Example 27, with suitable methyl carbimidothioate replacing methyl 25-difluorobenzenecarbimidothioate hydroiodide in the third stage.

Example 28

2-(2-bromophenyl)-6-{[2-(dimethylamino)ethyl]amino}-1,3-benzoxazole4,7-dione

The expected compound is obtained in the form of a pink powder. Melting point: 147-148° C.
MS-LC: MH+=390.12; r.t.=7.94 min.

Example 29

2-(3-bromophenyl)-6-{[2-(dimethylamino)ethyl]amino}-1,3-benzoxazole4,7-dione

The expected compound is obtained in the form of a red powder. Melting point: 174-175° C.
MS-LC: MH+=390.21; r.t.=8.10 min.

Example 30

2-(3-chlorophenyl)-6-{[2-(dimethylamino)ethyl]amino}-1,3-benzoxazole4,7-dione

The expected compound is obtained in the form of a red powder. Melting point: 174-175° C.
MS-LC: MH+=346.21; r.t.=8.20 min.

Example 31

2-(4-bromophenyl)-6-{[2-(dimethylamino)ethyl]amino}-1,3-benzoxazole-4,7-dione

The expected compound is obtained in the form of a red powder. Melting point: 181-182° C.
MS-LC: MH+=390.13; r.t.=8.37 min.

Example 32

2-(3,5-dibromophenyl)-6-{[2-(dimethylamino)ethyl]
amino}-1,3-benzoxazole-4,7-dione The expected compound is obtained in the form of a red powder. Melting point: 206-207° C.
MS-LC: MH+=468.03; r.t.=8.74 min.

Example 33

6-{[2-(dimethylamino)ethyl]amino}-2-(4-fluorophenyl)-1,3-benzoxazole4,7-dione

The expected compound is obtained in the form of a red powder. Melting point: 169-170° C.
MS-LC: MH+=330.26; r.t.=7.79 min.

Example 34

2-(3,5-difluorophenyl)-6-{[2-(dimethylamino)ethyl]
amino}-1,3-benzoxazole-4,7-dione The expected compound is obtained in the form of a red powder. Melting point: 176-177° C.
MS-LC: MH+=348.19; r.t.=7.91 min.

Example 35

2-(2,3-difluorophenyl)-6-{[2-(dimethylamino)ethyl]
amino}-1,3-benzoxazole-4,7-dione The expected compound is obtained in the form of a red powder. Melting point: 178-179° C.
MS-LC: MH+=348.25; r.t.=7.84 min.

Example 36

6-{[2-(dimethylamino)ethyl]amino}-2-(3,4,5-trifluorophenyl)-1,3-benzoxazole4,7-dione The expected compound is obtained in the form of a red powder. Melting point: 188-189° C.
MS-LC: MH+=366.17; r.t.=8.06 min.

Example 37

2-(4-bromo-3-methylphenyl)-6-{[2-(dimethylamino)
ethyl]amino}-1,3-benzoxazole-4,7-dione The expected compound is obtained in the form of a red powder. Melting point: 165-166° C.
MS-LC: MH+=404.13; r.t.=8.67 min.

Example 38

6-{[2-(dimethylamino)ethyl]amino}-2-(4-ethylphenyl)-1,3-benzoxazole-4,7-dione

The expected compound is obtained in the form of a red powder. Melting point: 151-152° C.
MS-LC: MH+=340.20; r.t.=8.19 min.

Example 39

2-(4-bromo-2-chlorophenyl)-6-{[2-(dimethylamino)
ethyl]amino}-1,3-benzoxazole4,7-dione The expected compound is obtained in the form of a red powder. Melting point: 163-164° C.
MS-LC: MH+=424.12; r.t.=8.36 min.

Example 40

6-{[2-(dimethylamino)ethyl]amino}-2-(3,4,5-trimethoxyphenyl)-1,3-benzoxazole-4,7-dione The expected compound is obtained in the form of a brown powder.
MS-LC: MH+=402.26; r.t.=7.78 min.

Example 41

2-(3,4-dimethoxyphenyl)-6-{[2-(dimethylamino)
ethyl]amino}-1,3-benzoxazole-4,7-dione The expected compound is obtained in the form of a black powder. Melting point: 181-182° C.
MS-LC: MH+=372.27; r.t.=7.70 min.

Example 42

2-(2,6-dichlorobenzyl)-6-{[2-(dimethylamino)ethyl]
amino}-1,3-benzoxazole4,7-dione The expected compound is obtained in the form of a red powder. Melting point: 172-173° C.
MS-LC: MH+=394.08; r.t.=8.19 min.

Example 43

2-(2-chloro-6-fluorobenzyl)-6-{[2-(dimethylamino)
ethyl]amino}-1,3-benzoxazole4,7-dione The expected compound is obtained in the form of a red powder. Melting point: 178-179° C.
MS-LC: MH+=378.17; r.t.=8.21 min.

Example 44

6-{[2-(dimethylamino)ethyl]amino}-2-(1-naphthylmethyl)-1,3-benzoxazole-4,7-dione The expected compound is obtained in the form of a red powder. Melting point: 153-154° C.
MS-LC: MH+=376.24; r.t.=8.42 min.

The compounds of Examples 45 to 59 are obtained in a similar manner to that described for Example 27, with suitable methyl carbimidothioate replacing methyl 2,5-difluorobenzenecarbimidothioate hydroiodide in the third stage and N-(2-aminoethyl)pyrrolidine replacing N,N-dimethylethylenediamine in the last stage.

Example 45

2-(2-bromophenyl)-6-[(2-pyrrolidin-1-ylethyl)
amino]-1,3-benzoxazole-4,7-dione

The expected compound is obtained in the form of a red powder. Melting point: 123-124° C.
MS-LC: MH+=416.13; r.t.=8.04 min.

Example 46

2-(3-bromophenyl)-6-[(2-pyrrolidin-1-ylethyl)amino]-1,3-benzoxazole-4,7-dione

The expected compound is obtained in the form of a red powder. Melting point: 163-164° C.
MS-LC: MH+=416.22; r.t.=8.21 min.

Example 47

2-(3-chlorophenyl)-6-[(2-pyrrolidin-1-ylethyl)amino]-1,3-benzoxazole4,7-dione

The expected compound is obtained in the form of a red powder. Melting point: 161-162° C.
MS-LC: MH+=372.14; r.t.=8.27 min.

Example 48

2-(4-bromophenyl)-6-[(2-pyrrolidin-1-ylethyl)amino]-1,3-benzoxazole-4,7-dione

The expected compound is obtained in the form of a red powder. Melting point: 165-166° C.
MS-LC: MH+=416.16; r.t.=8.50 min.

Example 49

2-(3,5-dibromophenyl)-6-[(2-pyrrolidin-1-ylethyl)amino]-1,3-benzoxazole-4,7-dione The expected compound is obtained in the form of a red powder. Melting point: 202-203° C.
MS-LC: MH+=494.04; r.t.=8.90 min.

Example 50

2-(4-fluorophenyl)-6-[(2-pyrrolidin-1-ylethyl)amino]-1,3-benzoxazole-4,7-dione

The expected compound is obtained in the form of a red powder. Melting point: 170-171° C.
MS-LC: MH+=356.24; r.t.=7.92 min.

Example 51

2-(3,5-difluorophenyl)-6-[(2-pyrrolidin-1-ylethyl)amino]-1,3-benzoxazole-4,7-dione The expected compound is obtained in the form of a red powder. Melting point: 163-164° C.
MS-LC: MH+=374.20; r.t.=8.02 min.

Example 52

6-[(2-pyrrolidin-1-ylethyl)amino]-2-(3,4,5-trifluorophenyl)-1,3-benzoxazole4,7-dione The expected compound is obtained in the form of a black powder. Melting point: 171-172° C.
MS-LC: MH+=392.17; r.t.=8.20 min.

Example 53

2-(4-bromo-3-methylphenyl)-6-[(2-pyrrolidin-1-ylethyl)amino]-1,3-benzoxazole-4,7-dione The expected compound is obtained in the form of a red powder. Melting point: 171-172° C.
MS-LC: MH+=430.14; r.t.=8.78 min.

Example 54

2-(4-ethylphenyl)-6-[(2-pyrrolidin-1-ylethyl)amino]-1,3-benzoxazole-4,7-dione

The expected compound is obtained in the form of a red powder. Melting point: 176-177° C.
MS-LC: MH+=266.24; r.t.=8.36 min.

Example 55

2-(4-bromo-2-chlorophenyl)-6-[(2-pyrrolidin-1-ylethyl)amino]-1,3-benzoxazole-4,7-dione The expected compound is obtained in the form of a red powder. Melting point: 153-154° C.
MS-LC: MH+=450.14; r.t.=8.49 min.

Example 56

6-[(2-pyrrolidin-1-ylethyl)amino]-2-(3,4,5-trimethoxyphenyl)-1,3-benzoxazole-4,7-dione The expected compound is obtained in the form of a brown powder.
MS-LC: MH+=428.27; r.t.=7.90 min.

Example 57

2-(3,4-dimethoxyphenyl)-6-[(2-pyrrolidin-1-ylethyl)amino]-1,3-benzoxazole-4,7-dione The expected compound is obtained in the form of a red powder. Melting point: 198.5-199.5° C.
MS-LC: MH+=398.26; r.t.=7.93 min.

Example 58

2-(2-chloro-6-fluorobenzyl)-6-[(2-pyrrolidin-1-ylethyl)amino]-1,3-benzoxazole-4,7-dione The expected compound is obtained in the form of a red powder. Melting point: 173-174° C.
MS-LC: MH+=404.16; r.t.=8.33 min.

Example 59

2-(1,3-benzodioxol-5-yl)-6-[(2-pyrrolidin-1-ylethyl)amino]-1,3-benzoxazole4,7-dione The expected compound is obtained in the form of a brown powder. Melting point: 171-172° C.
MS-LC: MH+=382.15; r.t.=7.95 min.

The compound of Example 60 is obtained in a similar manner to that described for Example 13, with n-hexylboronic acid replacing 2-naphthalene boronic acid in the third stage.

Example 60

6-{[2-(dimethylamino)ethyl]amino}-2-hexyl-1,3-benzothiazole-4,7-dione

The expected compound is obtained in the form of a red powder.

MS-LC: MH+=336.17; r.t.=8.29 min.

Pharmacological Study of the Compounds of the Invention

Test Protocols i) Measurement of the Phosphatase Activity of the Purified Cdc25C Recombinant Enzyme The phosphatase activity of the MBP-Cdc25C protein is evaluated by dephosphorylation of 3-O-methylfluorescein-phosphate (OMFP) to 3-O-methylfluorescein (OMF) with determination of the fluorescence of the reaction product at 475 nm. This test allows identification of the inhibitors of Cdc25 recombinant enzyme. The preparation of the fusion protein MBP-Cdc25C is described in PCT Patent Application WO 01/44467.

The reaction is carried out in 384-well plate format in a final volume of 50 µl. The MBP-Cdc25C protein (prepared as described above) is stored in the following elution buffer: 20 mM Tris-HCl pH 7.4; 250 mM NaCl; 1 mM EDTA; 1 mM of dithiothreitol (DTT); 10 mM maltose. It is diluted to a concentration of 60 µM in the following reaction buffer: 50 mM Tris-HCl pH 8.2; 50 mM NaCl; 1 mM DTT; 20% glycerol. Measurement of the background noise is carried out with the buffer without addition of the enzyme. The products are tested at decreasing concentrations starting from 40 µM. The reaction is initiated by the addition of an OMFP solution at 500 µM final (prepared extemporaneously from a 12.5 mM stock solution in 100% DMSO (Sigma #M2629)). After 4 hours at 30° C. in a disposable 384-well plate, the fluorescence measured at OD 475 nm is read using a Victor$^2$ plate reader (EGG-Wallac). Determination of the 50% inhibitory concentration of the enzymatic reaction is calculated from three independent experiments. Only the values included in the linear part of the sigmoid are retained for linear regression analysis.

ii) Measurement of the Tyrosine Phosphatase Activity of the CD45 Enzyme:

Measurement of the tyrosine phosphatase activity of CD45 is based on the dephosphorylation of the peptide pp60$^{c-src}$ by CD45. Only the cytoplasmic domain of purified human CD45 enzyme (amino acids 584 to 1281, molecular weight=95 kDa) expressed in a yeast expression system is used for the measurement. The substrate is a synthetic peptide based on the sequence of the negative regulatory domain of pp60$^{c-src}$. The released phosphate is measured by a malachite green type reagent.

The reaction is carried out in 384-well plate format with a final volume of 20 µl. The substrate pp60$^{c-src}$ (P-301, BIOMOL, Plymouth Meeting, Pa., USA) is diluted to a concentration of 925 µM in the following reaction buffer: 50 mM Hepes pH 7.2; 1 mM EDTA; 1 mM of dithiothreitol (DTT); 0.05% NP-40 surfactant. The final substrate concentration is 185 µM. The candidate products are tested in a range of decreasing concentrations starting from 160 µM. The reaction is initiated by adding CD45 (SE-135, BIOMOL, Plymouth Meeting, Pa., USA) at 15 U/µl (1 U=1 pmol/min) diluted in reaction buffer. The final enzyme concentration is 1.75 U/µl. After incubation for 1 hour at 30° C., BIOMOL Green Reagent (AK-111, BIOMOL, Plymouth Meeting, Pa., USA) is added in a volume of 50 µl/well. After 20 to 30 minutes during which the colour develops, the absorbance at 620 nm is read using a Victor$^2$ plate reader (EGG-Wallac). Determination of the 50% inhibitory concentration of the enzyme reaction is calculated from three independent experiments.

iii) Characterization of the Antiproliferative Activity:

By way of example, the effect of a treatment on two human cell lines Mia-Paca2 and DU145 by the compounds of the examples described previously will be studied. The cell lines DU145 (human prostate cancer cells) and Mia-PaCa2 (human pancreas cancer cells) were acquired from the American Tissue Culture Collection (Rockville, Md., USA). The cells placed in 80 µl of Dulbecco's Modified Eagle's medium (Gibco-Brl, Cergy-Pontoise, France) completed with 10% foetal calf serum inactivated by heating (Gibco-Brl, Cergy-Pontoise, France), 50,000 units/l of penicillin and 50 mg/l of streptomycin (Gibco-Brl, 10378-057, Cergy-Pontoise, France), and 2 mM of glutamine (Gibco-Brl, Cergy-Pontoise, France) were seeded on a 96-well plate on day 0. The cells were treated on day 1 for 96 hours with increasing concentrations of each of the compounds to be tested up to 10 µM. At the end of this period, quantification of cell proliferation is evaluated by a colorimetric test based on the cleavage of the tetrazolium salt WST1 by the mitochondrial dehydrogenases in viable cells leading to the formation of formazan (Boehringer Mannheim, Meylan, France). These tests are carried out in duplicate with 8 determinations per concentration tested. For each compound to be tested, the values included in the linear part of the sigmoid were retained for a linear regression analysis and used to estimate the inhibitory concentration IC$_{50}$. The products are solubilized in dimethylsulphoxide (DMSO) at 10$^{-2}$ M and finally used in culture with 0.1% DMSO.

Results of the Tests a) The compounds of Examples 1 to 60 have an IC$_{50}$ less than or equal to 10 µM on the phosphatase activity of the purified Cdc25-C recombinant enzyme.

b) The compounds of Examples 1 to 60 have an IC$_{50}$ less than or equal to 10 µM on the cell proliferation of the Mia-Paca2 lines.

c) The compounds of Examples 1 to 60 have a IC$_{50}$ less than or equal to 10 µM on the cell proliferation of the DU-145 lines.

The invention claimed is:

1. A compound selected from the group consisting of:
   2-(2,6-difluorophenyl)-5-{[2-(dimethylamino)ethyl]amino}-1,3-benzothiazole-4,7-dione;
   2-(2,5-dichlorothien-3-yl)-5-{[2-(dimethylamino)ethyl]amino}-1,3-benzothiazole-4,7-dione;
   2-(2,5-dichlorothien-3-yl)-5-[(2-pyrrolidin-1-ylethyl)amino]-1,3-benzothiazole-4,7-dione;
   5-{[2-(dimethylamino)ethyl]amino}-2-(4-fluorophenyl)-1,3-benzothiazole-4,7-dione;
   2-(4-fluorophenyl)-5-[(2-pyrrolidin-1-ylethyl)amino]-1,3-benzothiazole-4,7-dione;
   2-(2-chloro-6-fluorophenyl)-5-{[2-(dimethylamino)ethyl]amino}-1,3-benzothiazole-4,7-dione;
   2-(2-chloro-6-fluorophenyl)-5-[(2-pyrrolidin-1-ylethyl)amino]-1,3-benzothiazole-4,7-dione;
   6-{[2-(dimethylamino)ethyl]amino}-2-(4-fluorophenyl)-1,3-benzothiazole-4,7-dione;
   6-{[2-(dimethylamino)ethyl]amino}-2-(1-naphthyl)-1,3-benzothiazole-4,7-dione;
   2-(1,1'-biphenyl-4-yl)-6-{[2-(dimethylamino)ethyl]amino}-1,3-benzothiazole-4,7-dione;

2-(4-butylphenyl)-6-{[2-(dimethylamino)ethyl]amino}-1,3-benzothiazole-4,7-dione;
2-(2-chloro-6-fluorophenyl)-6-{[2-(dimethylamino)ethyl]amino}-1,3-benzothiazole-4,7-dione;
6-{[2-(dimethylamino)ethyl]amino}-2-(2-naphthyl)-1,3-benzothiazole-4,7-dione;
2-(2,5-difluorophenyl)-6-{[2-(dimethylamino)ethyl]amino}-1,3-benzothiazole-4,7-dione;
2-(2,5-difluorophenyl)-5-{[2-(dimethylamino)ethyl]amino}-1,3-benzoxazole-4,7-dione;
2-(2-bromophenyl)-5-{[2-(dimethylamino)ethyl]amino}-1,3-benzoxazole-4,7-dione;
2-(3-bromophenyl)-5-{[2-(dimethylamino)ethyl]amino}-1,3-benzoxazole-4,7-dione;
5-{[2-(dimethylamino)ethyl]amino}-2-(4-fluorophenyl)-1,3-benzoxazole-4,7-dione;
2-(3,5-difluorophenyl)-5-{[2-(dimethylamino)ethyl]amino}-1,3-benzoxazole-4,7-dione;
2-(2,3-difluorophenyl)-5-{[2-(dimethylamino)ethyl]amino}-1,3-benzoxazole-4,7-dione;
5-{[2-(dimethylamino)ethyl]amino}-2-(3,4,5-trifluorophenyl)-1,3-benzoxazole-4,7-dione;
5-{[2-(dimethylamino)ethyl]amino}-2-(4-ethylphenyl)-1,3-benzoxazole-4,7-dione;
2-benzyl-5-{[2-(dimethylamino)ethyl]amino}-1,3-benzoxazole-4,7-dione;
2-(3-bromophenyl)-5-[(2-pyrrolidin-1-ylethyl)amino]-1,3-benzoxazole-4,7-dione;
2-(3,5-difluorophenyl)-5-[(2-pyrrolidin-1-ylethyl)amino]-1,3-benzoxazole-4,7-dione;
5-[(2-pyrrolidin-1-ylethyl)amino]-2-(3,4,5-trifluorophenyl)-1,3-benzoxazole-4,7-dione;
2-(2,5-difluorophenyl)-6-{[2-(dimethylamino)ethyl]amino}-1,3-benzoxazole-4,7-dione;
2-(2-bromophenyl)-6-{[2-(dimethylamino)ethyl]amino}-1,3-benzoxazole-4,7-dione;
2-(3-bromophenyl)-6-{[2-(dimethylamino)ethyl]amino}-1,3-benzoxazole-4,7-dione;
2-(3-chlorophenyl)-6-{[2-(dimethylamino)ethyl]amino}-1,3-benzoxazole-4,7-dione;
2-(4-bromophenyl)-6-{[2-(dimethylamino)ethyl]amino}-1,3-benzoxazole-4,7-dione;
2-(3,5-dibromophenyl)-6-{[2-(dimethylamino)ethyl]amino}-1,3-benzoxazole-4,7-dione;
6-{[2-(dimethylamino)ethyl]amino}-2-(4-fluorophenyl)-1,3-benzoxazole-4,7-dione;
2-(3,5-difluorophenyl)-6-{[2-(dimethylamino)ethyl]amino}-1,3-benzoxazole-4,7-dione;
2-(2,3-difluorophenyl)-6-{[2-(dimethylamino)ethyl]amino}-1,3-benzoxazole 4,7-dione;
6-{[2-(dimethylamino)ethyl]amino}-2-(3,4,5-trifluorophenyl}-1,3-benzoxazole-4,7-dione;
2-(4-bromo-3-methylphenyl)-6-{[2-(dimethylamino)ethyl]amino}-1,3-benzoxazole-4,7-dione;
6-{[2-(dimethylamino)ethyl]amino}-2-(4-ethylphenyl)-1,3-benzoxazole-4,7-dione;
2-(4-bromo-2-chlorophenyl)-6-{[2-(dimethylamino)ethyl]amino}-1,3-benzoxazole-4,7-dione;
6-{[2-(dimethylamino)ethyl]amino}-2-(3,4,5-trimethoxyphenyl)-1,3-benzoxazole-4,7-dione;
2-(3,4-dimethoxyphenyl)-6-{[2-(dimethylamino)ethyl]amino}-1,3-benzoxazole-4,7-dione;
2-(2,6-dichlorobenzyl)-6-{[2-(dimethylamino)ethyl]amino}-1,3-benzoxazole-4,7-dione;
2-(2-chloro-6-fluorobenzyl)-6-{[2-(dimethylamino)ethyl]amino}-1,3-benzoxazole-4,7-dione;
6-{[2-(dimethylamino)ethyl]amino}-2-(1-naphthylmethyl)-1,3-benzoxazole-4,7-dione;
2-(2-bromophenyl)-6-[(2-pyrrolidin-1-ylethyl)amino]-1,3-benzoxazole-4,7-dione;
2-(3-bromophenyl)-6-[(2-pyrrolidin-1-ylethyl)amino]-1,3-benzoxazole-4,7-dione;
2-(3-chlorophenyl)-6-[(2-pyrrolidin-1-ylethyl)amino]-1,3-benzoxazole-4,7-dione;
2-(4-bromophenyl)-6-[(2-pyrrolidin-1-ylethyl)amino]-1,3-benzoxazole-4,7-dione;
2-(3,5-dibromophenyl)-6-[(2-pyrrolidin-1-ylethyl)amino]-1,3-benzoxazole-4,7-dione;
2-(4-fluorophenyl)-6-[(2-pyrrolidin-1-ylethyl)amino]-1,3-benzoxazole-4,7-dione;
2-(3,5-difluorophenyl)-6-[(2-pyrrolidin-1-ylethyl)amino]-1,3-benzoxazole-4,7-dione;
6-[(2-pyrrolidin-1-ylethyl)amino]-2-(3,4,5-trifluorophenyl)-1,3-benzoxazole-4,7-dione;
2-(4-bromo-3-methylphenyl)-6-[(2-pyrrolidin-1-ylethyl)amino]-1,3-benzoxazole-4,7-dione;
2-(4-ethylphenyl)-6-[(2-pyrrolidin-1-ylethyl)amino]-1,3-benzoxazole-4,7-dione;
2-(4-bromo-2-chlorophenyl)-6-[(2-pyrrolidin-1-ylethyl)amino]-1,3-benzoxazole-4,7-dione;
6-[(2-pyrrolidin-1-ylethyl)amino]-2-(3,4,5-trimethoxyphenyl)-1,3-benzoxazole-4,7-dione;
2-(3,4-dimethoxyphenyl)-6-[(2-pyrrolidin-1-ylethyl)amino]-1,3-benzoxazole-4,7-dione;
2-(2-chloro-6-fluorobenzyl)-6-[(2-pyrrolidin-1-ylethyl)amino]-1,3-benzoxazole-4,7-dione;
2-(1,3-benzodioxol-5-yl)-6-[(2-pyrrolidin-1-ylethyl)amino]-1,3-benzoxazole-4,7-dione;
6-{[2-(dimethylamino)ethyl]amino}-2-hexyl-1,3-benzothiazole-4,7-dione;
and a pharmaceutical salt thereof.

2. A compound of claim 1, selected from the group consisting of:
2-(2-chloro-6-fluorophenyl)-5-{[2-(dimethylamino)ethyl]amino}-1,3-benzothiazole-4,7-dione;
6-{[2-(dimethylamino)ethyl]amino}-2-(2-naphthyl)-1,3-benzothiazole-4,7-dione;
6-{[2-(dimethylamino)ethyl]amino}-2-(4-ethylphenyl)-1,3-benzoxazole-4,7-dione;
and a pharmaceutical salt thereof.

3. A compound selected from the group consisting of:
2-(2,6-difluorophenyl)-5-{[2-(dimethylamino)ethyl]amino)}-1,3-benzothiazole-4,7-dione;
2-(2,5-dichlorothien-3-yl)-5-{[2-(dimethylamino)ethyl]amino}-1,3-benzothiazole-4,7-dione;
2-(2,5-dichlorothien-3-yl)-5-[(2-pyrrolidin-1-ylethyl)amino]-1,3-benzothiazole-4,7-dione;
5-{[2-(dimethylamino)ethyl]amino)}-2-(4-fluorophenyl)-1,3-benzothiazole-4,7-dione;
2-(4-fluorophenyl)-5-[(2-pyrrolidin-1-ylethyl)amino]-1,3-benzothiazole-4,7-dione;
2-(2-chloro-6-fluorophenyl)-5-{[2-(dimethylamino)ethyl]amino}-1,3-benzothiazole-4,7-dione;
2-(2-chloro-6-fluorophenyl)-5-[(2-pyrrolidin-1-ylethyl)amino]-1,3-benzothiazole-4,7-dione;
and a pharmaceutical salt thereof.

4. A pharmaceutical composition comprising a therapeutically effective amount of a compound of claim 1 and an inert pharmaceutical carrier.

* * * * *